United States Patent [19]
Ito et al.

[11] Patent Number: 6,018,070
[45] Date of Patent: Jan. 25, 2000

[54] TWO-RINGS-CONTAINING PHENYL ESTER COMPOUND AND ANTI-PERROELECTRIC LIQUID CRYSTAL COMPOSITION CONTAINING THE SAME

[75] Inventors: Maki Ito, Tsukuba; Tomoyuki Yui, Nagareyama; Masahiro Johno; Teruyo Tomiyama, both of Tsukuba; Hiroshi Mineta, Tsukuba; Yuki Motoyama, Tsukuba, all of Japan

[73] Assignee: Mitsubishi Gas Chemicals Company, Inc., Ibaraki-ken, Japan

[21] Appl. No.: 08/839,342

[22] Filed: Apr. 18, 1997

Related U.S. Application Data

[62] Division of application No. 08/575,131, Dec. 19, 1995, Pat. No. 5,660,762.

[30] Foreign Application Priority Data

| Dec. 20, 1994 | [JP] | Japan | 6-316810 |
| Jan. 31, 1995 | [JP] | Japan | 7-013856 |
| Apr. 19, 1995 | [JP] | Japan | 7-093693 |

[51] Int. Cl.$^7$ ............ C09K 19/20; C07C 69/76; C07C 41/00
[52] U.S. Cl. ............ 560/76; 568/626; 568/631; 252/299.67
[58] Field of Search ............ 252/299.67; 560/76; 568/626, 631

[56] References Cited

U.S. PATENT DOCUMENTS

| 5,110,496 | 5/1992 | Mogamiya et al. | 252/299.61 |
| 5,207,947 | 5/1993 | Suzuki et al. | 252/299.67 |
| 5,328,641 | 7/1994 | Aihara et al. | 252/299.62 |
| 5,352,382 | 10/1994 | Johno et al. | 252/299.65 |

FOREIGN PATENT DOCUMENTS

| 0422996 | 4/1991 | European Pat. Off. |
| 0517504 | 12/1992 | European Pat. Off. |
| 2204842 | 5/1974 | France |
| 62-181237 | 8/1987 | Japan |

OTHER PUBLICATIONS

Neubert, et al., "The Effect of Carbonyl Containing . . .", Mol. Cryst. Liq. Cryst., 1993, vol. 234, pp. 47–68.

Isozaki, et al., "Successive Phase Transitions . . .", Japanese Journal of Applied Physics, vol. 30, No. 9A, Part 2, pp. L1573–L1575 (1991).

Chemical Abstracts, vol. 107, No. 22, Abstr. No. 209495n (1987).

Johno, et al., "Smectic Layer Switching by an Electric Field . . .", Japanese Journal of Applied Physics, vol. 28, No. 1, Jan., 1990 pp. 119–120.

Chandani, et al., "Antiferroelectric Chiral Smectic Phases . . .", Japanese Journal of Applied Physics, vol. 28, No. 7, Jul., 1989, pp. 1265–1268.

Chandani, etal., "Novel Phases Exhibiting Tristable Switching . . .", Japanese Journal of Applied Physics, vol. 28, No. 7, Jul., 1990 pp. 1261–1264.

Chandani, et al., "Tristable Switching in the Surface Stabilized . . .", Japanese Journal of Applied Physics, vol. 27, No. 5, May, 1988, pp. 729–732.

Johno, et al., "Correspondence Between Smectic Layer Switching . . .", Japanese Journal of Applied Physics, vol. 29, No. 1, Jan., 1990 pp. 111–114.

Nakagawa, A Hysteresis Model for Antiferroelectric $SMC_A$ Phases, Japanese Journal of Applied Physics, vol. 30, No. 8, Aug., 1989 pp. 1759–1764.

Preprints of No. 4 Ferroelectric Liquid Crystal International Symposium, p. 77, 1993.

*Primary Examiner*—C. H. Kelly

[57] ABSTRACT

A two-rings-containing phenyl ester compound of the following general formula (1),

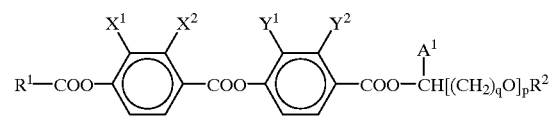

(1)

wherein $R^1$ is a linear alkyl group having 5 to 12 carbon atoms, $R^2$ is a linear alkyl group having 1 to 15 carbon atoms, $X^1$ and $X^2$ are both hydrogen atoms or one of $X^1$ and $X^2$ is a fluorine atom and the other is a hydrogen atom, $Y^1$ and $Y^2$ are both hydrogen atoms or one of $Y^1$ and $Y^2$ is a fluorine atom and the other is a hydrogen atom, and $A^1$ is a hydrogen atom, —$CH_3$ or —$CF_3$, provided that when $A^1$ is a hydrogen atom or —$CH_3$, p is 0 and that when $A^1$ is —$CF_3$, p is 1 and q is an integer of 5 to 8, and an anti-ferroelectric liquid crystal composition containing at least one of two-rings-containing phenyl ester compounds of the above general formula (1) in claim 1 and either an anti-ferroelectric liquid crystal compound or a mixture of anti-ferroelectric liquid crystal compounds.

4 Claims, No Drawings

TWO-RINGS-CONTAINING PHENYL ESTER COMPOUND AND ANTI-PERROELECTRIC LIQUID CRYSTAL COMPOSITION CONTAINING THE SAME

This is a division of application Ser. No. 08/575,131 filed Dec. 19, 1995 U.S. Pat. No. 5,660,762.

The present invention relates to a novel two-rings-containing phenyl ester compound, an anti-ferroelectric liquid crystal composition containing the above compound, and a liquid crystal display device for which the anti-ferroelectric liquid crystal is adapted.

A liquid crystal display device has been so far applied to various small-sized display devices owing to its low-voltage operability, low power consumption and small thickness of display portion. With recent broadening of application and use of liquid crystal display devices to/in an information and office automation-related machine and equipment field and a television field, there are rapidly rising demands for high-performance, large-sized liquid crystal display devices having display capacity and display quality over presently available CRT display devices.

However, so long as a present nematic liquid crystal is used, it is not at all easy to increase the size, and to decrease the cost, of even an active matrix driven liquid crystal display device that is used for a liquid crystal television nowaday, due to its complicated production process and low yield. Further, for a simple matrix driven STN liquid crystal display device, large capacity actuation is not necessarily easy, the response time has its limitation, and it is difficult to display an animation. Further, in a display device for which a nematic liquid crystal is adapted, its narrow viewing angle is recently a serious problem. Therefore it cannot be said at present that a nematic liquid crystal display device satisfies the above demands for a high-performance large-sized liquid crystal display device.

Under the circumstances, it is a liquid crystal display device using a ferroelectric liquid crystal that is attracting attention as a fast liquid crystal display device. It attracts attention that a surface stabilized ferroelectric liquid crystal (SSFLC) device disclosed by Clark and Lagerwall has a fast response speed and a wide viewing angle, and its switching characteristics has been studied in detail. A number of ferroelectric liquid crystals have been synthesized for optimizing various physical property constants. However, it has problems in that its threshold characteristic is insufficient, that its contrast is poor since its layer structure is a chevron structure, that no fast response is accomplished, that alignment control is difficult so that it is not easy to accomplish the bistability which is one of the greatest characteristics of SSFLC, and that alignment destroyed by mechanical impact is difficult to restore. It is required to overcome these problems for practical use.

In addition to this, the development of devices having switching mechanisms different from that of SSFLC are simultaneously under way. Switching of a liquid crystal substance having an anti-ferroelectric phase (to be referred to as "anti-ferroelectric liquid crystal substance" hereinafter) among tristable states is also one of these new switching mechanisms (Japanese Journal of Applied Physics, Vol. 27, pp. L729, 1988).

An anti-ferroelectric liquid crystal device has three stable states. That is, they are two uniform states (Ur, Ul) and a third state, observed in an anti-ferroelectric device. Chandani et al have reported that this third state is an anti-ferroelectric phase (Japanese Journal of Applied Physics, vol. 28, pp. L1261, 1989, Japanese Journal of Applied Physics, vol. 28, pp. L1265, 1989).

The above switching among tristable states is the first characteristic of an anti-ferroelectric liquid crystal device. The second characteristic of the anti-ferroelectric liquid crystal device is that a distinct threshold value is present relative to a charged voltage. Further, it has a memory effect, which is the third characteristic of the anti-ferroelectric liquid crystal device. By utilizing these excellent characteristics, a liquid crystal display device having a fast response speed and an excellent contrast can be achieved.

The anti-ferroelectric liquid crystal has another great characteristic in that that its layer structure easily performs switching on the basis of an electric field (Japanese Journal of Applied Physics, Vol. 28, pp. L119, 1989, Japanese Journal of Applied Physics, vol. 29, pp. L111, 1990).

On the basis thereof, a liquid crystal display device free of defects and capable of self-restoring alignment can be produced, and a liquid crystal device having an excellent contrast can be achieved.

Further, it has been demonstrated that voltage gradation which is almost impossible for a ferroelectric liquid crystal is possible for an anti-ferroelectric liquid crystal, it is made possible to shift toward a full-color display, and the importance of an anti-ferroelectric liquid crystal is increasing (Preprints of No. 4 Ferroelectric Liquid Crystal International Symposium, page 77, 1993).

As described above, an anti-ferroelectric liquid crystal is gaining reliable dominance, while it is desired to further improve its response speed.

Anti-ferroelectric liquid crystals which have been so far proposed have a response speed sufficient for achieving display devices at a certain level. However, when an attempt is made to achieve a high-definition display device whose number of scanning lines is at least 800, its response speed is not yet sufficient, and it is required to increase the response speed. Further, the serious problem with a liquid crystal device in general is that the response speed greatly depends upon temperature. This problems is also a burden on an anti-ferroelectric liquid crystal device, and it is strongly desired to decrease its temperature dependency.

For an anti-ferroelectric liquid crystal, there are two switching operations, one from an anti-ferroelectric state to a ferroelectric state and the other from a ferroelectric state to an anti-ferroelectric state. The speeds of these two switching operations by voltage, i.e., response speed, are important factors for determining a display quality.

The response speed particularly from an anti-ferroelectric state to a ferroelectric state (to be referred to as "response speed I" hereinafter) is important since it is, for example, a writing speed per a scanning line—line in simple matrix driving so that it determines the number of scanning lines which constitute one picture. That is, as the response speed I increases, the number of scanning lines can be increased, so that a high-definition device can be achieved.

Further, concerning the response speed from a ferroelectric state to an anti-ferroelectric state (to be referred to as "response speed II" hereinafter), a required speed alters depending upon a design of a drive method of the device. For example, it alters by the set voltage of an offset voltage. However, when the response speed II is too high, no ferroelectric state can be fully maintained (a light or dark state cannot be maintained). When it is too low, disadvantageously, no change from a ferroelectric state to an anti-ferroelectric state takes place (no rewriting from a light or dark state to a dark or light state can be performed).

That is, in the response speed II, an optimum response speed is set after a drive method is determined.

As explained above, a fast response speed I is important for achieving a high-definition device.

Anti-ferroelectric liquid crystals which have been already proposed have response speeds sufficient for achieving display devices at certain levels. However, for achieving a high-definition display device having a large number of scanning lines, their response speeds are not yet sufficient and are required to be further increased.

The problem of an anti-ferroelectric liquid crystal is to further increase its response speed, particularly to increase its response speed on a low-temperature side, as described above. Further, it is desirable to broaden the temperature range of the anti-ferroelectric phase and have a smetic A phase on a high-temperature side.

M. Nakagawa has shown that the response speed of an anti-ferroelectric liquid crystal depends upon the rotation viscosity of liquid crystal molecules (Masahiro Nakagawa, Japanese Journal of Applied Physics, 30, 1759 (1991)). That is, with a decrease in viscosity, the response speed increases.

When the response speed relative to temperature is observed, the response speed starts to decrease around room temperature and exponential-functionally decreases in the temperature range lower than room temperature. An anti-ferroelectric liquid crystal has a high viscosity since its liquid crystal phase is a smetic phase, so that its viscosity sharply increases on a low-temperature side, and it is considered that the response speed sharply decreases due to the viscosity resistance thereof.

In one method for overcoming the above problem, an attempt is being made to develop an anti-ferroelectric liquid crystal having a low viscosity, while anti-ferroelectric liquid crystal having a proper tilt angle, a proper response speed and the temperature range of an anti-ferroelectric phase and having a low viscosity has been not actually developed.

In another method, a device is provided with a heater. This method can reliably overcome the problem, while this method cannot be said to be practically advantageous since the production of a display device requires an additional cost and since the transmission decreases due to the heater.

In further another method, it is conceivable to make an attempt to synthesize a compound having a relatively low viscosity and add the compound to a liquid crystal composition to decrease the viscosity of the composition as a whole so as to improve the response speed, and this method is considered the most practical solution at present.

A substance used in the above method is naturally one having a low molecular weight. However, when the molecular weight is too low, disadvantageously, the substance which is added volatilizes and dissipates with time and the transition temperature of the composition from an isotropic phase to a liquid crystal phase is too low.

It is generally considered that when an anti-ferroelectric liquid crystal device is used as a display, the device has a temperature of at least about 40° C. due to backlight.

For normal driving of the device, therefore, the upper-limit temperature of the anti-ferroelectric phase is required to be at least 40° C., preferably at least 50° C. And, desirably, a smetic A phase for obtaining excellent alignment is practically present on the high-temperature side of this temperature.

Further, on the low-temperature side, the device is at least required to be driven at 10° C. The lower-limit temperature of the anti-ferroelectric phase is at least required to be 0° C.

The present invention has been made from the above point of view, and has been arrived at by finding the following. When a novel two-rings-containing phenyl ester compound of the general formula (1), having the following specific structure, is incorporated into an anti-ferroelectric liquid crystal, an anti-ferroelectric phase can be secured in a broad temperature range, a smetic A phase can be also allowed to be present at the same time, and an anti-ferroelectric liquid crystal composition which shows highly fast response speed at a low temperature can be obtained.

That is, according to the present invention, there is provided a two-rings-containing phenyl ester compound of the following general formula (1),

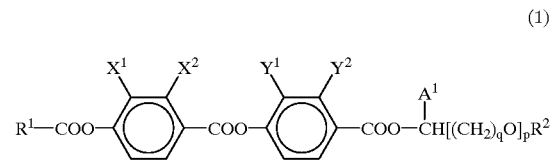

(1)

wherein $R^1$ is a linear alkyl group having 5 to 12 carbon atoms, $R^2$ is a linear alkyl group having 1 to 15 carbon atoms, $X^1$ and $X^2$ are both hydrogen atoms or one of $X^1$ and $X^2$ is a fluorine atom and the other is a hydrogen atom, $Y^1$ and $Y^2$ are both hydrogen atoms or one of $Y^1$ and $Y^2$ is a fluorine atom and the other is a hydrogen atom, and $A^1$ is a hydrogen atom, —$CH_3$ or —$CF_3$, provided that when $A^1$ is a hydrogen atom or —$CH_3$, p is 0 and that when $A^1$ is —$CF_3$, p is 1 and q is an integer of 5 to 8.

According to the present invention, further, there is provided an anti-ferroelectric liquid crystal composition prepared by incorporating the two-rings-containing phenyl ester compound of the general formula (1) into an anti-ferroelectric liquid crystal compound or a mixture of anti-ferroelectric liquid crystal compounds.

According to the present invention, furthermore, there is provided a simple matrix liquid crystal display device characterized in that an anti-ferroelectric liquid crystal composition containing the above two-rings-containing phenyl ester compound of the general formula (1) is held between one substrate having scanning electrodes disposed in a matrix form and the other substrate having signal electrodes disposed in a matrix form.

The two-rings-containing phenyl ester compound, the anti-ferroelectric liquid crystal composition and the simple matrix liquid crystal display device of the present invention will be explained further in detail hereinafter.

In the two-rings-containing phenyl ester compound of the general formula (1), the linear alkyl group as $R^1$ has 5 to 12 carbon atoms, preferably 8 to 12 carbon atoms. When a compound of the general formula (1) in which $R^1$ is a liner alkyl group having 7 carbon atoms or less, particularly 4 carbon atoms or less, is incorporated into an anti-ferroelectric liquid crystal or an anti-ferroelectric liquid crystal composition, there is a high effect on decreasing the viscosity and the response speed is greatly improved, while the tilt angle tends to be greatly decreased. When the number of carbon atoms is 13 or more, the compound of the general formula (1) shows a decreased effect on the response speed when incorporated into an anti-ferroelectric liquid crystal compound or a mixture of anti-ferroelectric liquid crystal compounds since the compound of the general formula (1) itself presumably has an increased viscosity.

When $A^1$ in the general formula (1) is a hydrogen atom, a compound of the general formula (1) in which p is 0 and $R^2$ is a linear alkyl group having 2 to 10 carbon atoms is preferred, and further, one which is the above compound and has a smetic A phase is further preferred. The substitution of fluorine atom on the phenyl group does not have any drastic effect. However, all of a compound of the general formula (1) in which $X^2$ is a fluorine atom and each of $X^1$, $Y^1$ and $Y^2$ is a hydrogen atom (Examples 27, 32) and a compound of the general formula (1) in which $Y^2$ is a fluorine atom and each of $X^1$, $X^2$ and $Y^1$ is a hydrogen atom (Examples 28–31) show a greater effect on the improvement of the response speed than that of any compound having no fluorine atom substituted.

In the two-rings-containing phenyl ester compound of the general formula (1), when A is —$CH_3$ or —$CF_3$, the carbon atom to which $A^1$ bonds is an asymmetric atom, and it can be an optically active compound. In this case, the chiral source used in the chiral portion of the compound of the general formula (1) includes 2-alkanols such as 2-hexanol, and 2-hexanol, 2-octanol and 2-decanol are commercially easily available.

When $A^1$ is —$CH_3$, preferred is a compound of the general formula (1) in which p is 0 and $R^2$ is a linear alkyl group having 3 to 8 carbon atoms. The effect of fluorine substitution on phenyl group is not much drastic. However, depending upon position of the fluorine substitution, the effect of the incorporation is greater than that of a non-substituted optical active compound.

That is, all of an optically active compound in which one of $X^1$ and $X^2$ is a fluorine atom and both $Y^1$ and $Y^2$ are hydrogen atoms (Examples 8–14, 23–25), an optically active compound in which both $X^1$ and $X^2$ are hydrogen atoms and one of $Y^1$ and $Y^2$ is a fluorine atom (Examples 15, 16, 26) and an optically active compound in which one of $X^1$ and $X^2$ is a fluorine atom and one of $Y^1$ and $Y^2$ is a fluorine atom (Examples 17–20) show a greater effect on the improvement of response speed than a non-substituted optically active compound.

However, these compounds are likely to relatively decrease the tilt angle, and are limited in this aspect. The most desirable compound which shows a small decrease in tilt angle and a great improvement in response speed when $A^1$ is —$CH_3$ is an optically active compound in which $X^2$ is a fluorine atom and all of $X^1$, $Y^1$ and $Y^2$ are hydrogen atoms (Examples 8–13, 23–25).

A compound in which p is 1, q is 5 and $R^2$ is ethyl (n=2) when $A^1$ is —$CF_3$ is preferred (Examples 21, 22), and further, a compound in which all of $X^1$, $X^2$, $Y^1$ and $Y^2$ are hydrogen atoms is preferred (Example 21).

The present invention uses an anti-ferroelectric liquid crystal composition prepared by mixing at least one of two-rings-containing phenyl ester compounds of the general formula (1) with an anti-ferroelectric liquid crystal compound or a mixture of anti-ferroelectric liquid crystal compounds. The mixing ratio is selected such that the anti-ferroelectric liquid crystal composition at least has an anti-ferroelectric phase in the temperature range of from 0° C. to 40° C., preferably in the temperature range of from −20° C. to +50° C.

The mixing proportion is difficult to uniformly determine, since the effect thereof differs depending upon the kind of the two-rings-containing phenyl ester compound selected or the kind of the anti-ferroelectric liquid crystal, while the amount of the two-rings-containing phenyl ester compound of the general formula (1) based on the weight or molar amount of the anti-ferroelectric compound or the mixture of anti-ferroelectric compounds is 1 to 70%, preferably 5 to 60%, particularly 10 to 50%.

In practical use, it is preferred to form a composition having a smetic A phase on a temperature side higher than a temperature at which it shows an anti-ferroelectric phase. When no smetic A phase is presents, the alignment properties are greatly poor, and it is difficult to obtain a high contrast.

The anti-ferroelectric liquid crystal compound(s), with which the two-rings-containing phenyl ester compound of the general formula (1) in the present invention is mixed, is/are particularly preferably anti-ferroelectric liquid crystal (s) of the following general formula (2).

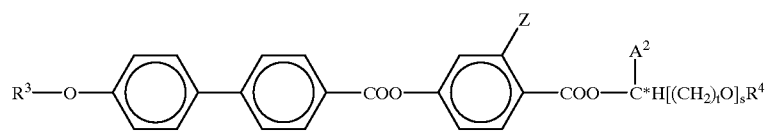

(2)

wherein $R^3$ is a linear alkyl group having 4 to 12 carbon atoms, $R^4$ is a linear alkyl group having 1 to 12 carbon atoms, Z is a hydrogen atom or a fluorine atom, $A^2$ is a —$CH_3$ or —$CF_3$, s is 0 or 1, t is an integer of 5 to 8, and $C^*$ is an asymmetric carbon, provided that when $A^2$ is —$CH_3$ and s is 0, $R^4$ is a linear alkyl group having 3 to 10 carbon atoms, that when $A^2$ is —$CF_3$ and s is 0, $R^4$ is a linear alkyl group having 4 to 8 carbon atoms, and that when $A^2$ is —$CF_3$ and s is 1, t is an integer of 5 to 8 and $R^4$ is a linear alkyl group having 1 to 6 carbon atoms.

In the anti-ferroelectric liquid crystal compound of the general formula (2), $R^3$ is preferably a linear alkyl group having 6 to 10 carbon atoms. When the number of carbon atoms is 5 or less, the temperature range of the anti-ferroelectric phase is narrow and the tilt angle is very small, so that the composition is not proper for practical use. When the number of carbon atoms exceeds 10, the viscosity of the composition of the general formula (2) itself is high, and it is therefore required to incorporate a large amount of the two-rings-containing phenyl ester compound, so that there arise other problems such as a decrease in tilt angle.

In the anti-ferroelectric liquid crystal compound of the general formula (2), preferred is an anti-ferroelectric liquid crystal compound in which $A^2$ is —$CH_3$, s is 0 and $R^4$ is a linear alkyl group having 4, 6 or 8 carbon atoms. Further, a compound of which the phenyl group has a fluorine substituent (Z in the general formula (2)) is preferred since it exhibits an anti-ferroelectric phase in a broader temperature range.

An anti-ferroelectric liquid crystal compound in which $A^2$ is —$CF_3$, s is 0 and $R^4$ is a linear alkyl group having 6 carbon atoms and an anti-ferroelectric liquid crystal compound in which $A^2$ is —$CF_3$, s is 1, t is 5 or 7 and $R^4$ is ethyl are preferred.

Particularly preferably, the anti-ferroelectric liquid crystal composition of the present invention at least has an anti-ferroelectric phase in the temperature range of from 0 to 40° C. and at least has a smetic A phase on a temperature side higher than a temperature at which it exhibits an anti-ferroelectric phase.

The anti-ferroelectric liquid crystal composition of the present invention has an anti-ferroelectric phase in a broad temperature range and is improved in the response speed, particularly in the response speed, from an anti-ferroelectric state to a ferroelectric state, and can be used for an anti-ferroelectric liquid crystal display device which can be suitably actuated in a broader temperature range.

That is, in a simple matrix liquid crystal display device having the anti-ferroelectric liquid crystal composition of the present invention held between substrates having scanning electrodes and signal electrodes disposed in a matrix form, the actuation by voltage can be performed by switching between one anti-ferroelectric state and two ferroelectric states.

The optically active 2-alkanols used for the synthesis of the compound of the general formula (1) in the present invention can be selected from commercially available ones. Further, optically active 1,1,1-trifluoro-7-ethoxy-2-heptanol and 1,1,1-trifluoro-8-ethoxy-2-octanol can be prepared by the method already disclosed by the present inventors (Japanese Laid-open Patent Publication No. 983/1992).

The process for producing the two-rings-containing phenyl ester compound of the general formula (1), provided by the present invention, is outlined by the following reaction scheme.

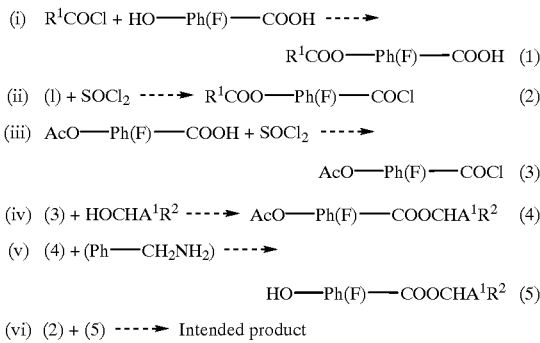

In the above reaction scheme, Ph(F) is a 1,4-phenylene group which may have a fluorine atom substituted on its position 2 or 3, AcO is an acetyl group ($CH_3COO-$), and $R^1$, $A^1$ and $R^2$ are as defined in the general formula (1).

The above production process will be briefly explained below.

(i) Ester (1) is prepared by reacting an aliphatic acid chloride with p-hydroxybenzoic acid which may have fluorine atom substituted on its ring.

(ii) The ester (1) is chlorinated with thionyl chloride.

(iii) Acetoxybenzoic acid is chlorinated with thionyl chloride.

(iv) Ester (4) is prepared by reacting the chloride in (3) with an alcohol (including an optically active alcohol).

(v) The ester (4) is deacetylated with benzylamine.

(vi) The chlorinated product (2) and the deacetylated product (5) are reacted.

Further, the anti-ferroelectric liquid crystal compound of the general formula (2) used for preparing the anti-ferroelectric liquid crystal composition in the present invention is produced by the following method.

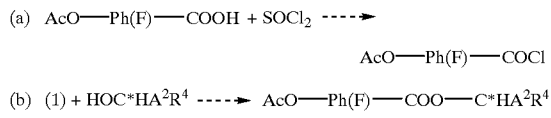

-continued

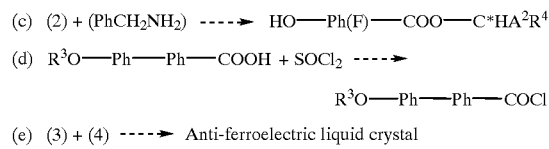

In the above reaction scheme, AcO— is a $CH_3COO-$ group, Ph(F) is a 1,4-phenylene group which may be substituted with a fluorine atom on its 3-position (Z=H or F in the general formula (2), $R^4$, $R^4$ and $A^2$ are as defined in the general formula (2), C* is asymmetric carbon, and Ph is a phenyl group or a 1,4-phenylene group.

The above production method will be briefly explained below.

(a) p-Acetoxybenzoic acid substituted or non-substituted with fluorine is chlorinated with thionyl chloride.

(b) The chlorinated product (a) and an optically active alcohol are reacted to form an ester.

(c) The ester (b) is deacetylated.

(d) Alkyloxybiphenylcarboxylic acid is chlorinated.

(e) Phenol (c) which is a deacetylation product of ester and the chlorinated product (d) are reacted to form a liquid crystal.

The present invention provides a novel two-rings-containing phenyl ester compound. When incorporated as one component for an anti-ferroelectric liquid crystal composition, the novel two-rings-containing phenyl ester compound increases the response speed of the composition in a broad temperature range. On the other hand, the novel two-rings-containing phenyl ester compound hardly impairs other properties, so that there can be provided an anti-ferroelectric liquid crystal display device having a high display quality in a broad temperature range.

EXAMPLES

The present invention will be explained further in detail with reference to Examples hereinafter, while the present invention shall not be limited to these Examples.

Example 1

R-4-(1-methylheptyloxycarbonyl)phenyl-4-n-undecanoyloxybenzoate (formula (1): $R^1=C_{10}H_{21}$, $A^1=CH_3$, $X^1$, $X^2$, $Y^1$, $Y^2=H$, p=0, $R^2=C_6H_{13}$ (E1))

(1) Preparation of 4-undecanoyloxybenzoic acid 12.7 Grams (0.0917 mol) of p-hydroxybenzoic acid was added to 150 ml of dichloromethane, and to this suspension was added 10.2 g (0.0917 mol) of triethylamine. The mixture was stirred until a homogeneous solution was formed. 19.7 Grams (0.096 mol) of undecanoyl chloride was added to the solution at such a rate that the dichloromethane was not refluxed. Then, 1.0 g (0.0085 mol) of 4-dimethylaminopyridine was added, and the mixture was stirred at room temperature overnight. 1N Hydrochloric acid was added to the reaction mixture and the mixture was subjected to extraction with ether. The ether was distilled off, and the resultant crude product was washed with hexane.

The crude product was dried to give 20.6 g (yield 85%) of the intended carboxylic acid.

(2) Preparation of 4-acetoxy-1-(1-methylheptyloxycarbonyl)benzene

Thionyl chloride in an amount of 60 ml was added to 10.8 g (0.06 mol) of 4-acetoxybenzoic acid, and the mixture was allowed to react under reflux for 7 hours. Then, excessive thionyl chloride was distilled off, and then 10 ml of pyridine and 5.24 g (0.0402 mol) of R-2-octanol were dropwise added. After the addition, the mixture was stirred at room temperature for a whole day, then diluted with 200 ml of ether, and an organic layer was consecutively washed with diluted hydrochloric acid, with a 1N sodium hydroxide aqueous solution and with water, and dried over magnesium sulfate. The solvent was distilled off, and the resultant crude intended product was purified by silica gel column chromatography using hexane/ethyl acetate as a solvent, to give 10.6 g (yield 90%) of the intended product.

(3) Preparation of 4-hydroxy-1-(1-methylheptyloxycarbonyl)benzene 10.6 Grams (0.0361 mol) of the compound obtained in the above (2) was dissolved in 250 ml of ethanol, and 7.74 g (0.0772 mol) of benzylamine was dropwise added. Further, the mixture was stirred at room temperature for a whole day, then diluted with 300 ml of ether, consecutively washed with diluted hydrochloric acid and with water, and dried over magnesium sulfate. The solvent was distilled off, and the residue was subjected to silica gel column chromatography for isolation and purification, to give 8.9 g (0.0356 mol) of the intended product (yield 98%).

(4) Preparation of R-4-(1-methylheptyloxycarbonyl)phenyl-4-n-undecanoyloxybenzoate Thionyl chloride in an amount of 15 ml was added to 3.1 mmol of the compound obtained in the above (1), and the mixture was refluxed under heat for 5 hours. Excessive thionyl chloride was distilled off, then 2 ml of pyridine and 2.12 mmol of the compound obtained in the above (3) were added, and the mixture was allowed to react at room temperature for 10 hours. After the completion of the reaction, the reaction mixture was diluted with 300 ml of ether, and consecutively washed with diluted hydrochloric acid, with a 1N sodium carbonate aqueous solution and with water, and an organic layer was dried over magnesium sulfate. Then, the solvent was distilled off, and the residue was subjected to silica gel column chromatography to isolate 0.99 g (0.00184 mol) of the end product (E1) (yield 87%). The end product was measured for physical properties, etc., and the measurement results are shown below. The end product was measured for physical properties, etc., and the measurement results are shown below.

Examples 2 and 3

Preparation of R-4-(1-methylpentyloxycarbonyl)phenyl-4-n-undecanoyloxybenzoate (formula (1): $R^1=C_{10}H_{21}$, $A^1=CH_3$, $X^1$, $X^2$, $Y^1$, $Y^2=H$, p=0, $R^2=C_4H_9$ (E2)) and R-4-(1-methylnonyloxycarbonyl)phenyl-4-n-undecanonyloxybenzoate (formula (1): $R^1=C_{10}H_{21}$, $A^1=CH_3$, $X^1$, $X^2$, $Y^1$, $Y^2=H$, p=0, $R^2=C_8H_{17}$ (E3))

End products were obtained in the same manner as in Example 1 except that R-2-octanol was replaced with R-2-hexanol or R-2-decanol.

The results of measurement for physical properties, etc., are shown below.

The chemical formulae of the intended products obtained in Examples 1 to 3 are shown below.

Table 1 shows H-NMR data of these compounds, and Table 2 shows results of measurement of their phase sequences.

The physical properties, etc., described below were measured as follows.

Phase identification was carried out by texture observation and DSC (differential scanning calorimeter) measurement.

Response speed and tilt angle were measured as follows. A liquid crystal cell (cell thickness 1.8 μm) having a rubbing-treated polyimide thin film and ITO electrodes was charged with a liquid crystal in an isotropic state. The cell was gradually cooled at a rate of 1° C./minute to align the liquid crystal in an SA phase. The cell was placed between polarization plates crossing at right angles such that the layer direction of the liquid crystal was in parallel with an analyzer or a polarizer. A step voltage of 35 V at a frequency of 10 Hz was applied to the liquid crystal cell, and the liquid crystal cell was measured for a response speed. The time required for transmitted light change changing from 10 to 90% was defined as a response time.

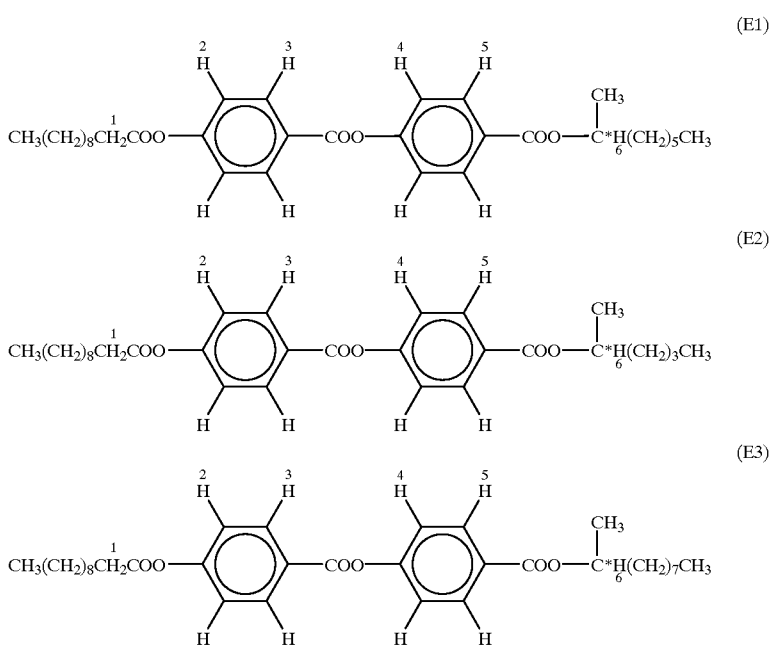

TABLE 1

H-NMR data of E1–E3

| Hydrogen atom number | 1 | 2 | 3 | 4 | 5 | 6 |
|---|---|---|---|---|---|---|
| E1 (ppm) | 2.6 | 7.3 | 8.3 | 7.2 | 8.1 | 5.2 |
| E2 (ppm) | 2.6 | 7.3 | 8.3 | 7.2 | 8.1 | 5.2 |
| E3 (ppm) | 2.6 | 7.3 | 8.3 | 7.2 | 8.1 | 5.2 |

TABLE 2

Phase sequence (E1–E3)

Phase sequence (parenthesized values = transition temperature (° C.))

| | | | | | |
|---|---|---|---|---|---|
| E1 | I (28) | SA (22) | SCA* (12) | Cr | |
| E2 | I (31) | SA (22) | SCY* (18) | SCA* (<0) | Cr |
| E3 | I (21) | SA (13.2) | SCA* (13) | Cr | |

Notes to Table 2
Parenthesized values=phase transition temperature (° C.).
The abbreviation in Table 2 are as follows.
I: isotropic phase,
SA: smectic A phase,
SCA*: anti-ferroelectric smectic C phase,
SIA*: anti-ferroelectric smectic I phase,
SCγ: ferrielectric phase, Cr: crystal phase

Examples 4–7

Preparation of R-4-(1-methylheptyloxycarbonyl)phenyl-4-n-nonanoyloxybenzoate (formula (1): $R^1=C_8H_{17}$, $A^1=CH_3$, $X^1$, $X^2$, $Y^1$, $Y^2$=H, p=0, $R^2=C_6H_{13}$ (E4)), R-4-(1-methylheptyloxycarbonyl)phenyl-4-n-decanoyloxybenzoate (formula (1): $R^1=C_9H_{19}$, $A^1=CH_3$, $X^1$, $X^2$, $Y^1$, $Y^2$=H, p=0, $R^2=C_6H_{13}$ (E5)), R-4-(1-methylheptyloxycarbonyl)phenyl-4-n-dodecanoyloxybenzoate (formula (1): $R^1=C_{11}H_{23}$, $A^1=CH_3$, $X^1$, $X^2$, $Y^1$, $Y^2$=H, p=0, $R^2=C_6H_{13}$ (E6)), and R-4-(1-methylheptyloxycarbonyl)phenyl-4-n-tridecanoyloxybenzoate (formula (1): $R^1=C_{12}H_{25}$, $A^1=CH_3$, $X^1$, $X^2$, $Y^1$, $Y^2$=H, p=0, $R^2=C_6H_{13}$ (E7))

The intended products were obtained in the same manner as in Example 1 except that the undecanoyl chloride in Example 1 was replaced with nonanoyl chloride, decanoyl chloride, dodecanoyl chloride or tridecanoyl chloride.

The results of measurement of physical properties, etc., are as follows. For abbreviations in Table 4, see notes to Table 2.

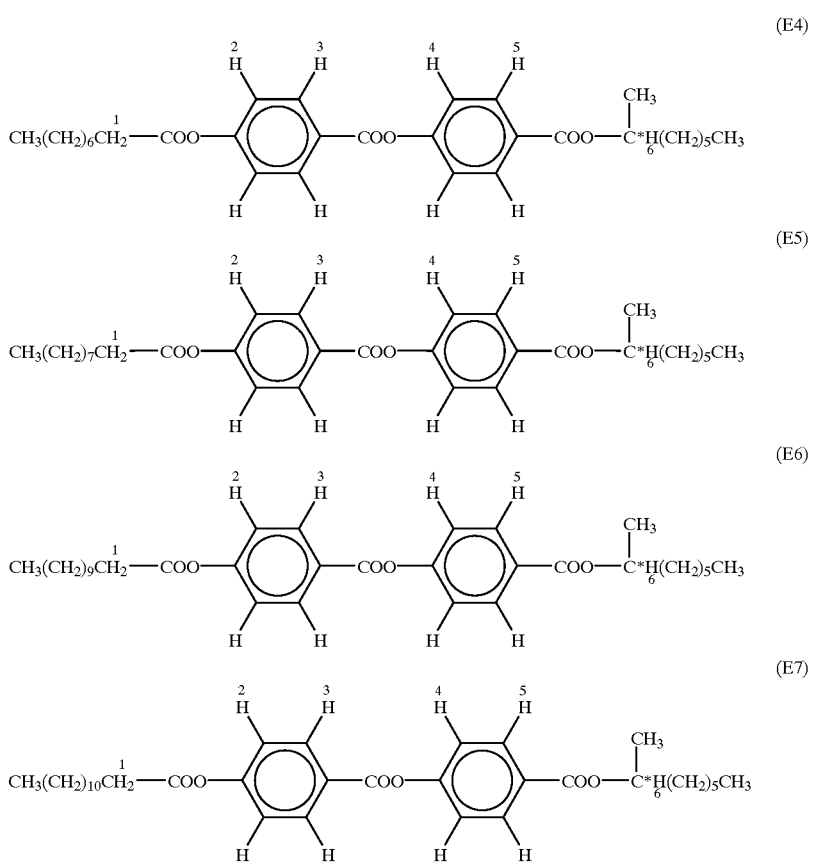

TABLE 3

H-NMR data of E4–E7

| Hydrogen atom number | 1 | 2 | 3 | 4 | 5 | 6 |
|---|---|---|---|---|---|---|
| E4 (ppm) | 2.6 | 7.3 | 8.3 | 7.2 | 8.1 | 5.2 |
| E5 (ppm) | 2.6 | 7.3 | 8.3 | 7.2 | 8.1 | 5.2 |
| E6 (ppm) | 2.6 | 7.3 | 8.3 | 7.2 | 8.1 | 5.2 |
| E7 (ppm) | 2.6 | 7.3 | 8.3 | 7.2 | 8.1 | 5.2 |

TABLE 4

Phase sequence (E4–E7)

Phase sequence (parenthesized values = transition temperature (° C.))

| | | | | |
|---|---|---|---|---|
| E4 | I (25) | Cr | | |
| E5 | I (27) | SA (10) | SCA* (0) | Cr |
| E6 | I (30) | SA (29.5) | Cr | |
| E7 | I (35) | Cr | | |

Example 8

Preparation of R-4-(1-methylheptyloxycarbonyl)phenyl-2-fluoro-4-n-undecanoyloxybenzoate (formula (1): $R^1=C_{10}H_{21}$, $A^1=CH_3$, $X^2=F$, $X^1$, $Y^1$, $Y^2=H$, p=0, $R^2=C_6H_{13}$ (E8))

The intended product was synthesized in the same manner as in Example 1 except that the 4-undecanoyloxybenzoic acid in Example 1 was replaced with 2-fluoro-4-undecanoyloxybenoic acid.

The results of measurement of physical properties, etc., are as follows. For abbreviations, see notes to Tables 1 and 2.

Examples 9 and 10

Preparation of R-4-(1-methylpentyloxycarbonyl)phenyl-2-fluoro-4-n-undecanoyloxybenzoate (formula (1): $R^1=C_{10}H_{21}$, $A^1=CH_3$, $X^2=F$, $X^1$, $Y^1$, $Y^2=H$, p=0, $R^2=C_4H_9$ (E9)) and R-4-(1-methylnonyloxycarbonyl)phenyl-2-fluoro-4-n-undecanoyloxybenzoate (formula (1): $R^1=C_{10}H_{21}$, $A^1=CH_3$, $X^2=F$, $X^1$, $Y^1$, $Y^2=H$, p=0, $R^2=C_8H_{17}$ (E10))

The intended products were obtained in the same manner as in Example 8 except that the R-2-octanol in Example 8 was replaced with R-2-hexanol or R-2-decanol.

The results of measurement of physical properties, etc., are as follows. For abbreviations, see notes to Tables 1 and 2.

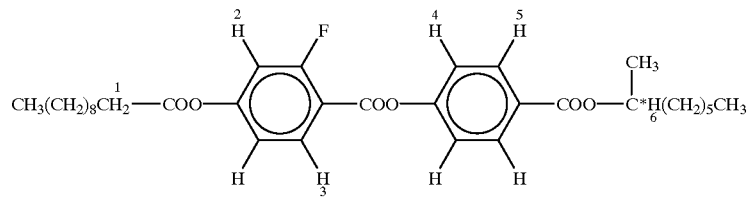

(E8)

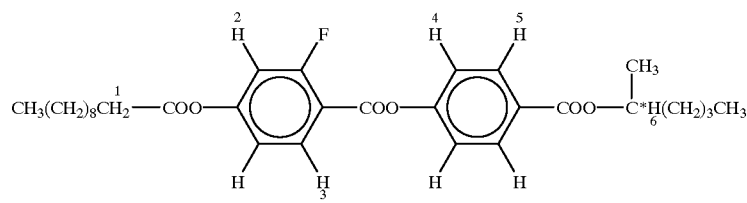

(E9)

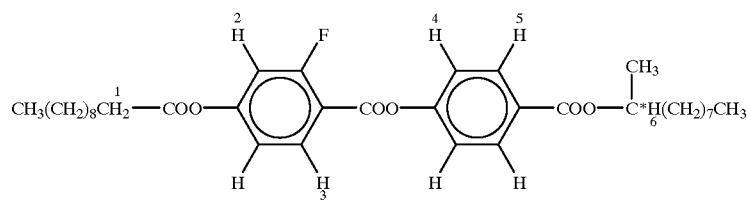

(E10)

TABLE 5

H-NMR data of E8–E10

| Hydrogen atom number | 1 | 2 | 3 | 4 | 5 | 6 |
|---|---|---|---|---|---|---|
| E8 (ppm) | 2.6 | 7.1 | 8.2 | 7.2 | 8.1 | 5.2 |
| E9 (ppm) | 2.6 | 7.1 | 8.2 | 7.2 | 8.1 | 5.2 |
| E10 (ppm) | 2.6 | 7.1 | 8.1 | 7.3 | 8.1 | 5.2 |

TABLE 6

Phase sequence (E8–E10)

| | | Phase sequence (parenthesized values = transition temperature (° C.)) | | |
|---|---|---|---|---|
| E8 | I (22) | SA (0.8) | SCA* (<0) | Cr |
| E9 | I (22) | SA (−12) | Cr | |
| E10 | I (18) | SA (8) | Cr | |

Examples 11–13

Preparation of R-4-(1-methylheptyloxycarbonyl)phenyl-2-fluoro-4-n-decanoyloxybenzoate (formula (1): $R^1=C_9H_{19}$, $A^1=CH_3$, $X^2=F$, $X^1$, $Y^1$, $Y^2=H$, p=0, $R^2=C_6H_{13}$ (E11)), R-4-(1-methylheptyloxycarbonyl)phenyl-2-fluoro-4-n-dodecanoyloxybenzoate (formula (1): $R^1=C_{11}H_{23}$, $A^1=CH_3$, $X^2=F$, $X^1$, $Y^1$, $Y^2=H$, p=0, $R^2=C_6H_{13}$ (E12)), and R-4-(1-methylheptyloxycarbonyl)phenyl-2-fluoro-4-n-tridecanoyloxybenzoate (formula (1): $R^1=C_{12}H_{25}$, $A^1=CH_3$, $X^2=F$, $X^1$, $Y^1$, $Y^2=H$, p=0, $R^2=C_6H_{13}$ (E13))

The intended products were obtained in the same manner as in Example 8 except that the 2-fluoro-4-undecanoyloxybenzoic acid in Example 8 was replaced with 2-fluoro-4-decanoyloxybenzoic acid (Example 11), 2-fluoro-4-dodecanoyloxybenzoic acid (Example 12) or 2-fluoro-4-tridecanoyloxybenzoic acid (Example 13).

The results of measurement of physical properties, etc., are as follows. For abbreviations, see notes to Tables 1 and 2.

TABLE 7

H-NMR data of E11–E13

| Hydrogen atom number | 1 | 2 | 3 | 4 | 5 | 6 |
|---|---|---|---|---|---|---|
| E11 (ppm) | 2.6 | 7.1 | 8.2 | 7.3 | 8.1 | 5.2 |
| E12 (ppm) | 2.6 | 7.1 | 8.2 | 7.3 | 8.1 | 5.2 |
| E13 (ppm) | 2.6 | 7.1 | 8.2 | 7.3 | 8.1 | 5.2 |

TABLE 8

Phase sequence (E11–E13)

| | | Phase sequence (parenthesized values = transition temperature (° C.)) | | |
|---|---|---|---|---|
| E11 | I (20) | SA (−29) | Cr | |
| E12 | I (25) | SA (15) | SCA* (13) | Cr |
| E13 | I (23) | SA (21) | Cr | |

Example 14

Preparation of R-4-(1-methylnonyloxycarbonyl)phenyl-3-fluoro-4-n-undecanoyloxybenzoate (formula (1): $R^1=C_{10}H_{21}$, $A^1=CH_3$, $X^1=F$, $X^2$, $Y^1$, $Y^2=H$, p=0, $R^2=C_8H_{17}$ (E14))

The intended product was obtained in the same manner as in Example 1 except that the 4-undecanoyloxybenzoic acid was replaced with 3-fluoro-4-undecanoyloxybenzoic acid and that the 2-octanol was replaced with 2-decanol.

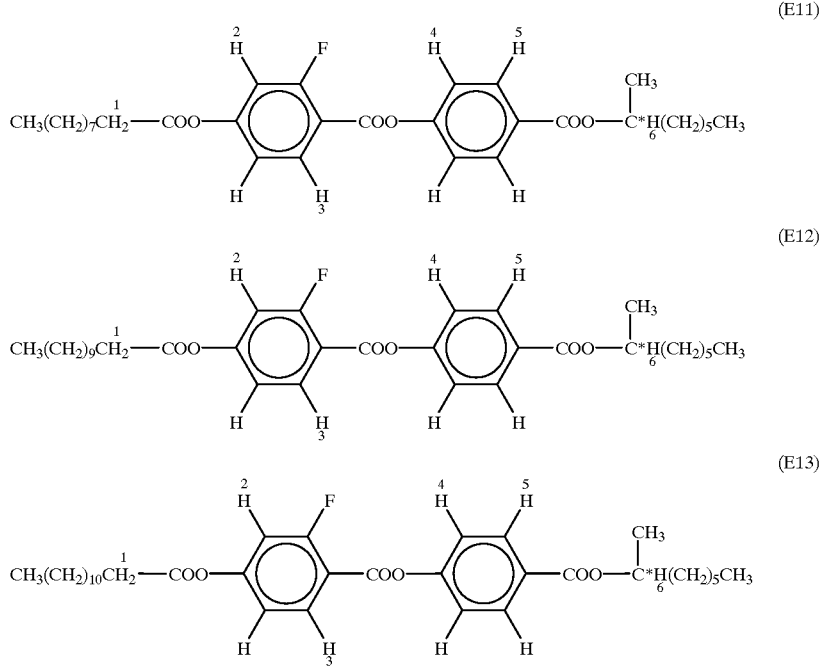

The results of measurement of physical properties, etc., are as follows. For abbreviations, see notes to Tables 1 and 2.

Example 15
Preparation of R-3-fluoro-4-(1-methylnonyloxycarbonyl) phenyl-4-n-undecanoyloxybenzoate (formula (1): $R^1=C_{10}H_{21}$, $A^1=CH_3$, $Y^2=F$, $X^1$, $X^2$, $Y^1=H$, $p=0$, $R^2=C_8H_{17}$ (E15))

The intended product was obtained in the same manner as in Example 1 except that the 4-acetoxybenzoic acid was replaced with 2-fluoro-4-acetoxybenzoic acid and that the 2-octanol was replaced with 2-decanol.

The results of measurement of physical properties, etc., are as follows. For abbreviations, see notes to Tables 1 and 2.

Example 16
Preparation of R-2-fluoro-4-(1-methylnonyloxycarbonyl) phenyl-4-n-undecanoyloxybenzoate (formula (1): $R^1=C_{10}H_{21}$, $A^1=CH_3$, $Y^1=F$, $X^1$, $X^2$, $Y^2=H$, $p=0$, $R^2=C_8H_{17}$ (E16))

The intended product was obtained in the same manner as in Example 1 except that the 4-acetoxybenzoic acid was replaced with 3-fluoro-4-acetoxybenzoic acid and that the 2-octanol was replaced with 2-decanol.

The results of measurement of physical properties, etc., are as follows. For abbreviations, see notes to Tables 1 and 2.

TABLE 10

Phase sequence (E14–16)

| | Phase sequence (parenthesized values = transition temperature (° C.)) | | | |
|---|---|---|---|---|
| E14 | I (5) | Cr | | |
| E15 | I (24) | SA (22) | SCA* (8) | Cr |
| E16 | I (3) | Cr | | |

Examples 17–20
Preparation of R-2-fluoro-4-(1-methylnonyloxycarbonyl) phenyl-3-fluoro-4-n-undecanoyloxybenzoate (formula (1): $R^1=C_{10}H_{21}$, $A^1=CH_3$, $X^1$, $Y^1=F$, $X^2$, $Y^2=H$, $p=0$, $R^2=C_8H_{17}$ (E17)), R-2-fluoro-4-(1-methylnonyloxycarbonyl)phenyl-2-fluoro-4-n-undecanoyloxybenzoate (formula (1): $R^1=C_{10}H_{21}$, $A^1=CH_3$, $X^2$, $Y^1=F$, $X^1$, $Y^2=H$, $p=0$, $R^2=C_8H_{17}$ (E18)), R-3-fluoro-4-(1-methylnonyloxycarbonyl)phenyl-3-fluoro-4-n-undecanoyloxybenzoate (formula (1): $R^1=C_{10}H_{21}$, $A^1=CH_3$, $X^1$, $Y^2=F$, $X^2$, $Y^1=H$, $p=0$, $R^2=C_8H_{17}$ (E19)), and R-3-fluoro-4-(1-methylnonyloxycarbonyl) phenyl-2-fluoro-4-n-undecanoyloxybenzoate (formula (1): $R^1=C_{10}H_{21}$, $A^1=CH_3$, $X^2$, $Y^2=F$, $X^1$, $Y^1=H$, $p=0$, $R^2=C_8H_{17}$ (E20))

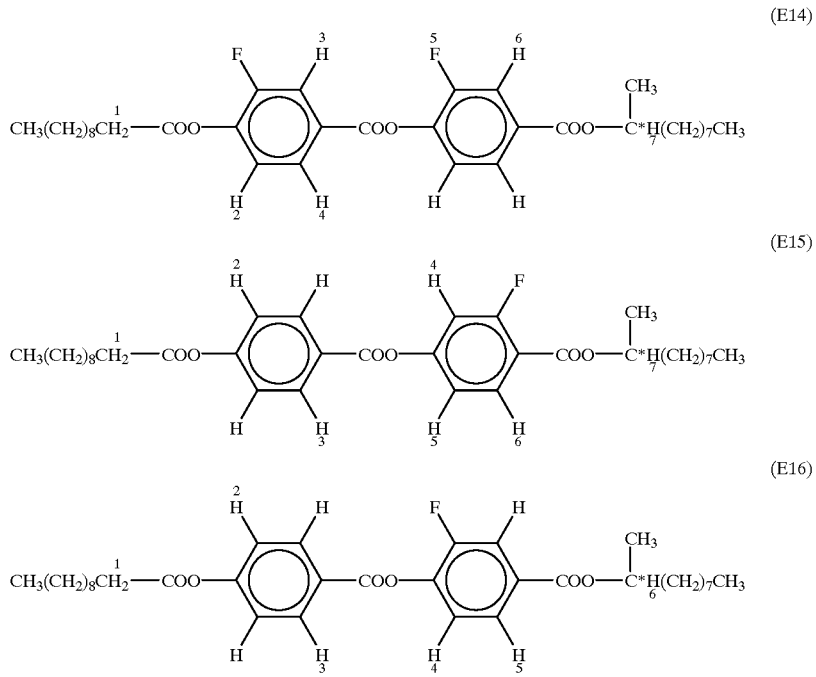

TABLE 9

H-NMR data of E14–E16

| Hydrogen atom number | 1 | 2 | 3 | 4 | 5 | 6 | 7 |
|---|---|---|---|---|---|---|---|
| E14 (ppm) | 2.6 | 7.3 | 8.0 | 8.0 | 7.3 | 8.2 | 5.2 |
| E15 (ppm) | 2.6 | 7.3 | 8.2 | 7.1 | 7.1 | 8.0 | 5.2 |
| E16 (ppm) | 2.6 | 7.2 | 8.3 | 7.3 | 7.9 | 5.2 | — |

The intended products were obtained in the same manner as in Example 1 except that the 4-acetoxybenozic acid was replaced with 2-fluoro-4-acetoxybenzoic acid and 3-fluoro-4-acetoxybenozic acid, that the p-hydroxybenzoic acid was replaced with 3-fluoro-4-hydroxybenzoic acid and 2-fluoro-4-hydroxybenzoic acid and that the 2-octanol was replaced with 2-decanol.

The results of measurement of physical properties, etc., are as follows. For abbreviations, see notes to Tables 1 and 2.

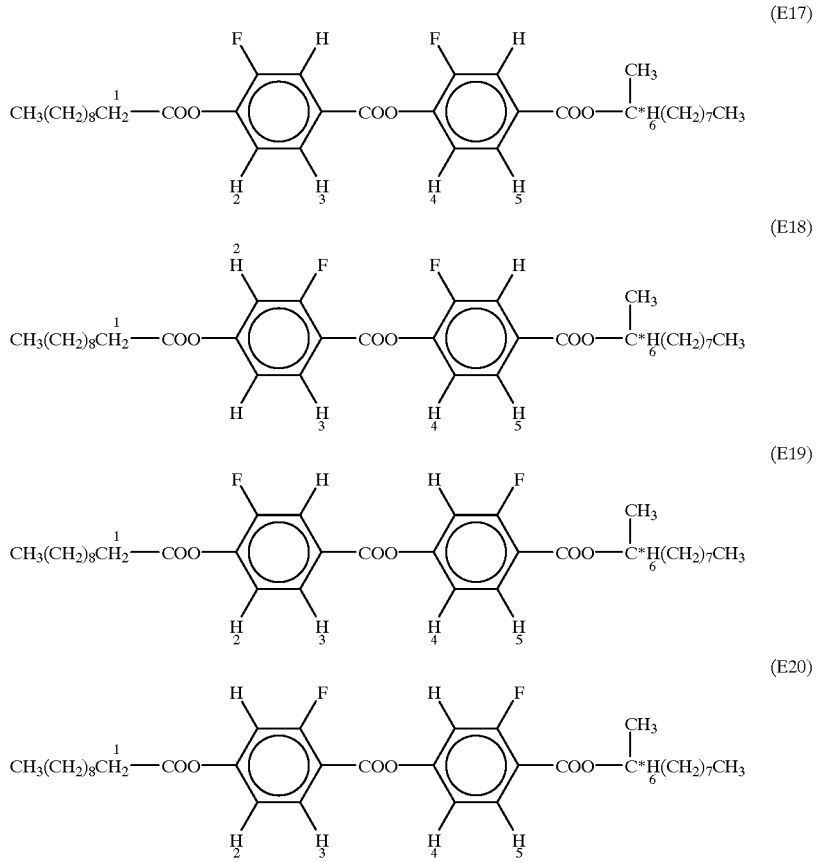

TABLE 11

H-NMR data of E17–E20

| Hydrogen atom number | 1 | 2 | 3 | 4 | 5 | 6 |
|---|---|---|---|---|---|---|
| E17 (ppm) | 2.6 | 7.3 | 8.1 | 7.3 | 8.0 | 5.2 |
| E18 (ppm) | 2.6 | 7.1 | 8.2 | 7.4 | 7.9 | 5.2 |
| E19 (ppm) | 2.6 | 7.3 | 8.0 | 7.1 | 8.0 | 5.2 |
| E20 (ppm) | 2.6 | 7.0 | 8.1 | 7.1 | 8.0 | 5.2 |

TABLE 12

Phase sequence (E17–E20)

Phase sequence (parenthesized values = transition temperature (° C.))

| E17 | I (−14) | Cr | | |
| E18 | I (6) | Cr | | |
| E19 | I (1) | SA (−7) | Cr | |
| E20 | I (19) | SA (13) | SCA* (1) | Cr |

Example 21

Preparation of R-4-(1-trifluoromethyl-6-ethoxyhexyloxycarbonyl)phenyl-4-n-undecanoyloxybenzoate (formula (1): $C_{10}H_{21}$, $A^1=CF_3$, $X^1$, $X^2$, $Y^1$, $Y^2=H$, p=1, q=5, $R^2=C_2H_5$ (E21))

An optically active compound was obtained in the same manner as in Example 1 except that the 2-octanol was replaced with 1,1,1-trifluoro-7-ethoxy-2-heptanol.

The results of measurement of physical properties, etc., are as follows. For abbreviations, see notes to Tables 1 and 2.

Example 22

Preparation of R-4-(1-trifluoromethyl-6-ethoxyhexyloxycarbonyl)phenyl-2-fluoro-4-n-undecanoyloxybenzoate (formula (1): $C_{10}H_{21}$, $A^1=CF_3$, $X^2=F$, $X^1$, $Y^1$, $Y^2=H$, p=1, q=5, $R^2=C_2H_5$ (E22))

An optically active compound was obtained in the same manner as in Example 8 except that the 2-octanol was replaced with 1,1,1-trifluoro-7-ethoxy-2-heptanol.

The results of measurement of physical properties, etc., are as follows. For abbreviations, see notes to Tables 1 and 2.

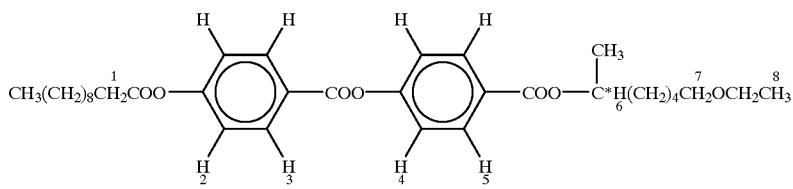

(E21)

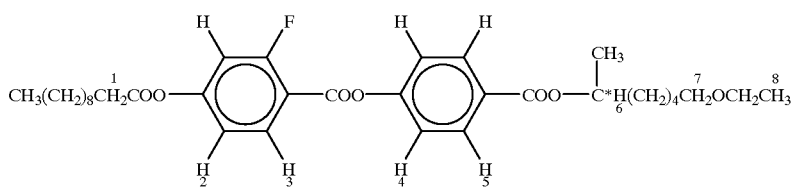

(E22)

TABLE 13

H-NMR data of E21 and E22

| Hydrogen atom number | 1 | 2 | 3 | 4 | 5 | 6 | 7 | 8 |
|---|---|---|---|---|---|---|---|---|
| E21 (ppm) | 2.6 | 7.3 | 8.2 | 7.2 | 8.1 | 5.6 | 3.4 | 1.2 |
| E22 (ppm) | 2.6 | 7.1 | 8.2 | 7.4 | 8.2 | 5.6 | 3.4 | 1.2 |

TABLE 14

Phase sequence (E21 and E22)

| | Phase sequence (parenthesized values = transition temperature (° C.)) | |
|---|---|---|
| E21 | I (−19) | Cr |
| E22 | I (−31) | Cr |

Examples 23–26

Preparation of R-4-(1-methylbutyloxycarbonyl)phenyl-2-fluoro-decanoyloxybenzoate (formula (1): $R^1=C_9H_{19}$, $X^2=F$, $X^1$, $Y^1$, $Y^2=H$, p=0, $A^1=CH_3$, $R^2=C_3H_7$ (E23)), R-4-(1-methylpentyloxycarbonyl)phenyl-2-fluoro-decanoyloxybenzoate (formula (1): $R^1=C_9H_{19}$, $X^2=F$, $X^1$, $Y^1$, $Y^2=H$, p=0, $A^1=CH_3$, $R^2=C_4H_9$ (E24)), R-4-(1-methylhexyloxycarbonyl)henyl-2-fluoro-decanoyloxybenzoate (formula (1): $R^1=C_9H_{19}$, $X^2=F$, $X^1$, $Y^1$, $Y^2=H$, p=0, $A^1=CH_3$, $R^2=C_5H_{11}$ (E25)), and R-4-(1-methyloctyloxycarbonyl)phenyl-2-fluoro-decanoyloxybenzoate (formula (1): $C_9H_{19}$, $Y^2=F$, $X^1$, $X^2$, $Y^1=H$, p=0, $A^1=CH_3$, $R^2=C_7H_{15}$ (E26))

The intended products were obtained in the same manner as in Example 1 except that the 4-undecanoyloxybenzoic acid was replaced with 2-fluoro-4-decanoyloxybenzoic acid (Examples 23–25) or 4-decanoyloxybenzoic acid (Example 26) and that the 4-hydroxy-1-(1-methylheptyloxycarbonyl) benzene was replaced with 4-hydroxy-1-(1-methylbutyloxycarbonyl)benzene (Example 23), 4-hydroxy-1-(1-methylpentyloxycarbonyl)benzene (Example 24), 4-hydroxy-1-(1-methylhexyloxycarbonyl) benzene (Example 25), or 4-hydroxy-1-(1-methyloctyloxycarbonyl)benzene (Example 26).

The results of measurement of physical properties, etc., are as follows. For abbreviations, see notes to Tables 1 and 2.

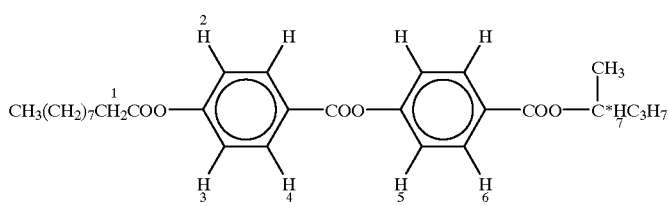

(E23)

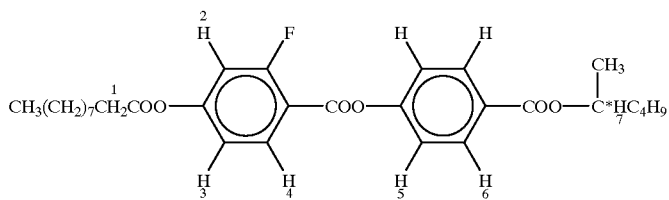

(E24)

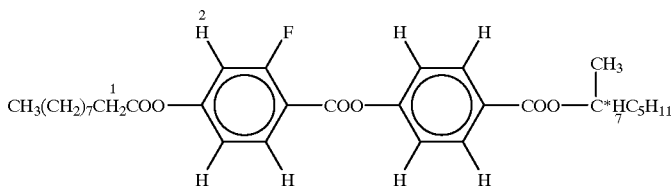

(E25)

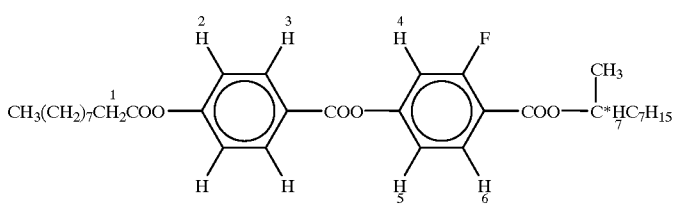

(E26)

TABLE 15

H-NMR data of E23–E26

| Hydrogen atom number | 1 | 2 | 3 | 4 | 5 | 6 | 7 |
|---|---|---|---|---|---|---|---|
| E23 (ppm) | 2.6 | 7.0 | 7.0 | 8.2 | 7.3 | 8.2 | 5.2 |
| E24 (ppm) | 2.6 | 7.1 | 7.1 | 8.1 | 7.3 | 8.1 | 5.2 |
| E25 (ppm) | 2.6 | 7.1 | 7.1 | 8.2 | 7.3 | 8.2 | 5.2 |
| E26 (ppm) | 2.6 | 7.3 | 8.2 | 7.1 | 7.1 | 8.0 | 5.3 |

TABLE 16

Phase sequence (E23–E26)

| | Phase sequence (parenthesized values = transition temperature (° C.)) | | | |
|---|---|---|---|---|
| E23 | I (27) | SA (1) | SCA* (−12) | Cr |
| E24 | I (25) | SA (−12) | SCAY* (−14) | Cr |
| E25 | I (21) | SA (−3) | SCA* (−18) | Cr |
| E26 | I (26) | SA (22) | SCA* (−8) | Cr |

Example 27

Preparation of 4-heptyloxycarbonylphenyl-2-fluoro-4-n-decanonyloxybenzoate (formula (1): $R^1=C_9H_{19}$, $X^2=F$, $X^1$, $Y^1$, $Y^2=H$, $A^1=H$, p=0, $R^2=C_6H_{13}$ (E27))

(1) Preparation of 4-decanoyloxy-2-fluorobenzoic acid 15.6 Grams (0.1 mol) of 4-hydroxy-2-fluorobenzoic acid was dissolved in 140 ml of dichloromethane. To the mixture were consecutively added 16 ml of triethylamine, 0.1 g (0.11 mol) of n-decanoic acid chloride and 0.97 (0.0079 mol) of dimethylaminopyridine, and the mixture was stirred at room temperature for a whole day. 10% Hydrochloric acid in an amount of 50 ml was added, and the mixture was subjected to extraction with 100 ml of ether three times. The organic layer was washed with a sodium chloride aqueous solution three times and dried over anhydrous sodium sulfate. The solvent was distilled off, the residue was washed with 400 ml of hexane to give 25.5 g of the intended product.

(2) Preparation of 4-acetoxy-1-heptyloxycarbonylbenzene 3.5 Grams of 4-acetoxybenzoic acid was added to 25 ml of thionyl chloride, and the mixture was allowed to react under reflux for 10 hours. Then, excessive thionyl chloride was distilled off, 10 ml of pyridine and 50 ml of toluene were then added, and 1.5 g of n-heptanol was dropwise added. After the addition, the mixture was refluxed under heat for 4 hours, and then the reaction mixture was allowed to cool and diluted with 500 ml of dichloromethane. An organic layer was consecutively washed with diluted hydrochloric acid, with a 1N sodium hydroxide aqueous solution and with water, and dried over magnesium sulfate. Further, the solvent was distilled off to give 1.7 g of the crude intended product.

(3) Preparation of 4-hydroxy-1-heptyloxycarbonylbenzene 1.7 Grams of the crude product obtained in (2) was dissolved in 50 ml of ethanol, and 4 g of benzylamine was dropwise added. Further, the mixture was stirred at room temperature for 4 hours, then diluted with 500 ml of chloroform, consecutively washed with diluted hydrochloric acid and with water, and dried over magnesium sulfate. The solvent was distilled off, and the product was isolated and purified by silica gel column chromatography to give 0.9 g of the intended product.

(4) Preparation of 4-heptyloxycarbonylphenyl-2-fluoro-4-n-decanonyloxybenzoate (1) Thionyl chloride in an amount of 10 ml was added to 0.5 g (0.0017 mol) of the 4-decanoyloxybenzoic acid obtained in (1), and the mixture was refluxed under heat for 4 hours. The thionyl chloride was distilled off, and the resultant acid chloride was dissolved in 0.52 g of toluene. To the mixture were consecutively added 0.35 g (0.0015 mol) of the 4-hydroxy-1-heptyloxycarbonylbenzene obtained in (3) and 0.27 g (0.0034 mol) of pyridine, and the mixture was stirred at room temperature for 24 hours. Water in an mount of 10 ml was added, the mixture was stirred for 30 minutes, 20 ml of 1N hydrochloric acid was added, and the mixture was extracted with 20 ml of dichloromethane twice. An organic layer was washed with 20 ml of water, and dried over anhydrous sodium sulfate. The solvent was distilled off to give 0.60 g of a crude product. The crude product was purified by silica gel column chromatography to give 0.43 g of the intended product (to be referred to as "E27" hereinafter).

Table 17 shows the NMR data of the so-obtained intended product and the result of crystal phase identification thereof.

Example 28

Preparation of 3-fluoro-4-heptyloxycarbonylphenyl-4-n-decanoyloxybenzoate (formula (1): $R^1=C_9H_{19}$, $Y^2=F$, $X^1$, $X^2$, $Y^1=H$, $A^1=H$, p=0, $R^2=C_6H_{13}$ (E28))

The intended product (to be referred to as "-E28" hereinafter) was obtained in the same manner as in Example 27 except that the 4-hydroxy-2-fluorobenzoic acid and the p-acetoxybenzoic acid were replaced with 4-hydroxybenzoic acid and 2-fluoro-4-acetoxybenzoic acid.

Table 17 shows the NMR data of the so-obtained intended product and the result of crystal phase identification thereof.

Examples 29–33

Preparation of 3-fluoro-4-undecyloxycarbonylphenyl-4-n-decanoyloxybenzoate (formula (1): $R^1=C_9H_{19}$, $Y^2=F$, $X^1$, $X^2$, $Y^1=H$, $A^1=H$, p=0, $R^2=C_{10}H_{21}$ (E29)), 3-fluoro-4-nonyloxycarbonylphenyl-4-n-decanoyloxybenzoate (formula (1): $R^1=C_9H_{19}$, $Y^2=F$, $X^1$, $X^2$, $Y^1=H$, $A^1=H$, p=0, $R^2=C_8H_{17}$ (E30)), 3-fluoro-4-propyloxycarbonylphenyl-4-n-decanoyloxybenzoate (formula (1): $R^1=C_9H_{19}$, $Y^2=F$, $X^1$, $X^2$, $Y^1=H$, $A^1=H$, p=0, $R^2=C_2H_5$ (E31)), 4-nonyloxycarbonylphenyl-2-fluoro-4-n-decanoyloxybenzoate (formula (1): $R^1=C_9H_{19}$, $X^2=F$, $X^1$, $Y^1$, $Y^2=H$, $A^1=H$, p=0, $R^2=C_8H_{17}$ (E32)) and 4-nonyloxycarbonylphenyl-4-n-decanoyloxybenzoate (formula (1): $R^1=C_9H_{19}$, $X^1-Y^2=H$, $A^1=H$, p=0, $R^2=C_8H_{17}$ (E33))

The above compounds (E29–E33) were synthesized according to Example 27.

Table 17 shows the NMR data of the intended product and the result of crystal phase identification thereof.

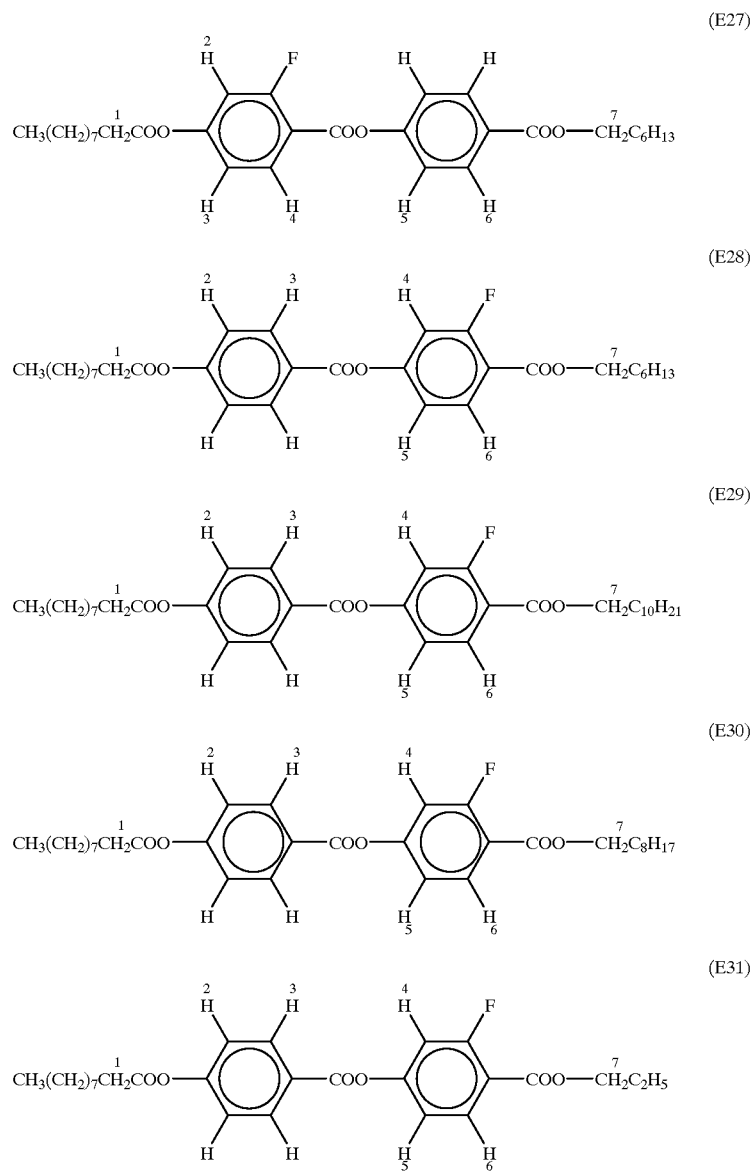

-continued

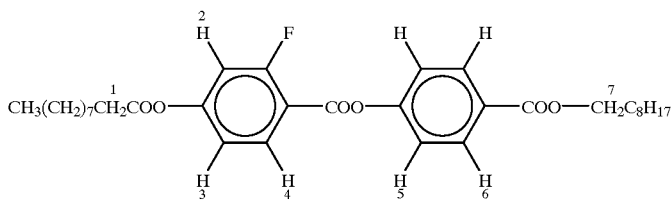
(E32)

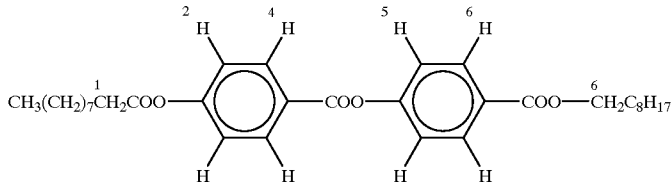
(E33)

TABLE 17

| | Hydrogen atom number of the formulae (ppm) | | | | | | |
|---|---|---|---|---|---|---|---|
| | 1 | 2 | 3 | 4 | 5 | 6 | 7 | Phase sequence |
| E27 | 2.6 | 7 | 7 | 8.2 | 7.3 | 8.1 | 4.4 | I (61) SA (33) Cr |
| E28 | 2.6 | 7.2 | 8.2 | 7.1 | 7.1 | 8 | 4.4 | I (71) SA (37) Cr |
| E29 | 2.6 | 7.3 | 8.2 | 7.1 | 7.1 | 8 | 4.4 | I (70) SA (37) Cr |
| E30 | 2.6 | 7.3 | 8.2 | 7.1 | 7.1 | 8 | 4.4 | I (71) SA (37) Cr |
| E31 | 2.6 | 7.3 | 8.2 | 7.1 | 7.1 | 8 | 4.4 | I (77) SA (44) Cr |
| E32 | 2.6 | 7.0 | 7.0 | 8.2 | 7.3 | 8.1 | 4.4 | I (68) SA (42) Cr |
| E33 | 2.6 | 7.3 | 8.3 | 7.3 | 8.1 | 4.4 | — | I (77) SA (37) Cr |

Examples 34–36

The above-obtained optically active compound E1, E2 or E3 in an amount of 30 wt % was added to the following anti-ferroelectric liquid crystal A (to be referred to as AF1 hereinafter), and each of the resultant compositions was measured for a phase sequence, a response speed, a tilt angle, etc. Tables 18 and 19 show the results.

AF1: n-$C_8H_{17}$—O—Ph—Ph—COO—Ph(3F)—COO—C*H($CH_3$)$C_6H_{13}$

In the above formula, Ph is a 1,4-phenylene group, Ph(3F) is a 1,4-phenylene group substituted with F on its 3 position (Z=F in formula (2)), and C* is asymmetric carbon.

Each composition were measured for physical properties, etc., as follows.

Phase identification was carried out by texture observation and DSC (differential scanning calorimeter) measurement. The response speed and the tilt angle were measured as follows. A liquid crystal cell (cell thickness 1.8 μm) having a rubbing-treated polyimide thin film and ITO electrodes was charged with a composition in an isotropic state. The cell was gradually cooled at a rate of 1° .C/minute to align the liquid crystal in an SA phase. The cell was placed between polarization plates crossing at right angles such that the layer direction of the liquid crystal was in parallel with an analyzer or a polarizer. A step voltage of 35 V at a frequency of 10 Hz was applied to the liquid crystal cell, and the liquid crystal cell was measured for a response speed. The time required for transmitted light change changing from 10 to 90% was defined as a response time.

The cell was rotated by applying a triangular voltage of 0.2 Hz±40V, and the tilt angle was determined on the basis of its rotation angle.

Examples 37–40

The optically active compounds E4 to E7 obtained in Examples 4 to 7, in an amount of 30 wt % each, were respectively added to AF1, and each of the resultant compositions was measured for a phase sequence, a response speed, a tilt angle, etc., in the same manner as in Example 35. Tables 18 and 19 show the results.

Parenthesized values in Table 18 show temperatures (° C.) of phase transition. Abbreviations stand for the following.
I: isotropic phase,
SA: smectic A phase,
SCA*: anti-ferroelectric smectic C phase
SIA*: anti-ferroelectric smectic I phase,
SCγ *: ferridielectric phase,
Cr: crystal phase

TABLE 18

| | Phase sequence (parenthesized values = transition temperature (° C.)) | Com-ponent | Weight ratio |
|---|---|---|---|
| Liquid crystal | | | |
| AF1 | I (140) SA (121) SCA* (20) SIA* (<0) Cr | | |
| Ex. 34 | I (104) SA (79) SCA* (<0) Cr | AF1/E1 | = 70/30 |
| Ex. 35 | I (106) SA (79) SCA* (<0) Cr | AF1/E2 | = 70/30 |
| Ex. 36 | I (105) SA (79) SCA* (<0) Cr | AF1/E3 | = 70/30 |
| Ex. 37 | I (100) SA (69) SCA* (<0) Cr | AF1/E4 | = 70/30 |
| Ex. 38 | I (106) SA (79) SCA* (<0) Cr | AF1/E5 | = 70/30 |
| Ex. 39 | I (106) SA (81) SCA* (<0) Cr | AF1/E6 | = 70/30 |
| Ex. 40 | I (104) SA (80) SCA* (<0) Cr | AF1/E7 | = 70/30 |

TABLE 19

| Measured | Response speed I | | | Response speed II | | | Tilt angle | | |
|---|---|---|---|---|---|---|---|---|---|
| temp. (° C.) | 60 | 40 | 20 | 60 | 40 | 20 | 60 | 40 | 20 |
| Liquid crystal | | | | | | | | | |
| AF1 | 854 | 1305 | 1935 | 611 | 2145 | 7885 | 29.9 | 29.4 | 28 |
| Ex. 34 | 10 | 69 | 223 | 378 | 1300 | 6910 | 26 | 27 | 27 |
| Ex. 35 | 16 | 215 | 732 | 147 | 690 | 2950 | 24 | 26 | 26 |
| Ex. 36 | 7 | 27 | 115 | 241 | 360 | 1950 | 25 | 26 | 26 |
| Ex. 37 | 5 | 14 | 75 | 130 | 484 | 2780 | 20 | 23 | 24 |
| Ex. 38 | 7 | 31 | 177 | 282 | 1000 | 6910 | 24 | 26 | 26 |
| Ex. 39 | 22 | 123 | 252 | 450 | 1360 | 8190 | 26 | 28 | 26 |
| Ex. 40 | 34 | 185 | 418 | 468 | 1710 | 5340 | 27 | 28 | 29 |

Notes)

Response speed I: speed from anti-ferroelectric state to ferroelectric state, unit $\mu$ second.

Response speed II: speed from ferroelectric state to anti-ferroelectric state, unit $\mu$ second.

In Table 18, the anti-ferroelectric phase of the liquid crystal AF1 is in the temperature range of from 121° C.–20° C., and the lower-limit temperature of the anti-ferroelectric phase of this liquid crystal is as high as 20° C., so that it can be actuated only at a temperature of at least 20° C. In contrast, each of the liquid crystal compositions containing 30 wt % of the optically active compounds E1 to E7 has a lower-limit temperature of 0° C. or lower, and shows the temperature range of anti-ferroelectric phase preferred as a display device.

Further, in the response speed I from an anti-ferroelectric state to a ferroelectric state, the liquid crystal AF1 shows a low response speed and has a problem in practical use. On the other hand, the anti-ferroelectric liquid crystal compositions obtained by incorporating 30 wt % of the optically active compounds E1 to E7 into the liquid crystal AF1 have greatly increased response speeds I and can be practically used, but the optically active compound E4 shows a relatively strong negative effect on decreasing the tilt angle.

Examples 41–46

The optically active compounds E8 to E13 obtained in Examples 8 to 13, in an amount of 30 wt % each, were respectively added to AF1, and each of the resultant compositions was measured for a phase sequence, a response speed, a tilt angle, etc., in the same manner. Tables 20 and 21 show the results.

TABLE 20

| Liquid crystal | Phase sequence (parenthesized values = transition temperature (° C.)) | Component | Weight ratio |
|---|---|---|---|
| Ex. 41 | I (108) SA (81) SCA* (<0) Cr | AF1/E8 | = 70/30 |
| Ex. 42 | I (106) SA (72) SCA* (<0) Cr | AF1/E9 | = 70/30 |
| Ex. 43 | I (100) SA (66) SCA* (<0) Cr | AF1/E10 | = 70/30 |
| Ex. 44 | I (94) SA (63) SCA* (<0) Cr | AF1/E11 | = 70/30 |
| Ex. 45 | I (99) SA (70) SCA* (<0) Cr | AF1/E12 | = 70/30 |
| Ex. 46 | I (99) SA (71) SCA* (<0) Cr | AF1 E13 | = 70/30 |

Notes)

For abbreviations, see notes to Table 18.

TABLE 21

| Measured | Response speed I | | | Response speed II | | | Tilt angle | | |
|---|---|---|---|---|---|---|---|---|---|
| temp. (° C.) | 60 | 40 | 20 | 60 | 40 | 20 | 60 | 40 | 20 |
| Liquid crystal | | | | | | | | | |
| AF1 | 854 | 1305 | 1935 | 611 | 2145 | 7885 | 29.9 | 29.4 | 28 |
| Ex. 41 | 8 | 40 | 140 | 281 | 922 | 5440 | 25 | 27 | 27 |
| Ex. 42 | 6 | 53 | 307 | 120 | 431 | 2740 | 20 | 24 | 25 |
| Ex. 43 | 6 | 13 | 54 | 138 | 657 | 1760 | 19 | 24 | 25 |
| Ex. 44 | | 11 | 43 | | 665 | 2900 | | 22 | 23 |
| Ex. 45 | | 5 | 35 | | 447 | 1560 | 23 | 26 | 27 |
| Ex. 46 | 6 | 26 | | 540 | 1120 | | 23 | 27 | 27 |

Notes)

Response speed I: speed from anti-ferroelectric state to ferroelectric state, unit $\mu$ second.

Response speed II: speed from ferroelectric state to anti-ferroelectric state, unit $\mu$ second.

Example 45: The upper-limit temperature of SCA* was so low that the measurement at 60° C. was not carried out.

Examples 46 and 47: The alignment state was defective so that the measurement at 20° C. was not carried out.

As is clearly shown in Table 21, the optically active compounds E8 to E13 show remarkable effects on the improvement of the anti-ferroelectric liquid crystal in response speed, particularly on the improvement in the response speed from an anti-ferroelectric state to a ferroelectric state, but the compound E10 shows a somewhat strong negative effect on decreasing the tilt angle.

Examples 47 and 48

The optically active compounds E14 and E16 obtained in Examples 14 and 16, in an amount of 30 wt % each, were respectively added to AF1, and each of the resultant compositions was measured for a phase sequence, a response speed, a tilt angle, etc., in the same manner. Tables 22 and 23 show the results.

As is clearly shown in Table 23, the optically active compounds E14 and E16 show remarkable effects on the improvement of the anti-ferroelectric liquid crystal in response speed, particularly on the improvement in the response speed from an anti-ferroelectric state to a ferroelectric state, but these compounds show a somewhat strong negative effect on decreasing the tilt angle.

Referential Example 1

The optically active compound E15 obtained in Example 15, in an amount of 30 wt %, was added to a liquid crystal AF1, and the mixture was measured for a phase sequence, a response speed, a tilt angle, etc. Tables 22 and 23 show the results.

The response speed on the low-temperature side is low instead of being increased.

TABLE 22

| | Phase sequence (parenthesized values = transition temperature (° C.)) | Component | Weight ratio |
|---|---|---|---|
| E47 | I (95) SA (64) SCY* (59) SCA* (<0) Cr | AF1/E14 | = 70/30 |
| E48 | I (98) SA (60) SCA* (<0) Cr | AF1/E16 | = 70/30 |
| Ref. Ex. 1 | I (105) SA (79) SCY* (77) SCA* (<0) Cr | AF1 E15 | = 70/30 |

Notes)
For abbreviations, see notes to Table 18.

TABLE 23

| Measured | Response speed I | | | Response speed II | | | Tilt angle | | |
|---|---|---|---|---|---|---|---|---|---|
| temp. (° C.) | 60 | 40 | 20 | 60 | 40 | 20 | 60 | 40 | 20 |
| E47 | | 9 | 36 | | 827 | 2140 | | 20 | 22 |
| E48 | | 12 | 52 | | 949 | 4890 | | 21 | 23 |
| Ref. Ex. 1 | 34 | 526 | 4350 | 266 | 824 | 3230 | 26 | 28 | 28 |

Notes)
Response speed I: speed from anti-ferroelectric state to ferroelectric state, unit $\mu$ second.
Response speed II: speed from ferroelectric state to anti-ferroelectric state, unit $\mu$ second.
Examples 47 and 48: The upper-limit temperature of SCA* was low so that the measurement at 60° C. was not carried out.

Examples 49–52

The optically active compounds E17 to E20 obtained in Examples 17 to 20, in an amount of 30 wt % each, were respectively added to a liquid crystal AF1, and each of the resultant compositions was measured for a phase sequence, a response speed, a tilt angle, etc., in the same manner as in Example 34. Tables 24 and 25 show the results.

As shown in Table 25, the optically active compounds E17 to E20 show remarkable effects on the improvement of the anti-ferroelectric liquid crystal in response speed, particularly on the improvement in the response speed from an anti-ferroelectric state to a ferroelectric state, but the optically active compounds E17 to E19 also show a negative effect on decreasing the tilt angle.

TABLE 24

| | Phase sequence (parenthesized values = transition temperature (° C.)) | Component | Weight ratio |
|---|---|---|---|
| E49 | I (89) SA (82) SCY* (78) SCA* (<0) Cr | AF1/E17 | = 70/30 |
| E50 | I (97) SA (67) SCY* (62) SCA* (<0) Cr | AF1/E18 | = 70/30 |
| E51 | I (91) SA (69) SCY* (66) SCA* (<0) Cr | AF1/E19 | = 70/30 |
| E52 | I (100) SA (70) SCY* (67) SCA* (<0) Cr | AF1/E20 | = 70/30 |

Notes)
For abbreviations, see notes to Table 18.

TABLE 25

| Measured | Response speed I | | | Response speed II | | | Tilt angle | | |
|---|---|---|---|---|---|---|---|---|---|
| temp. (° C.) | 60 | 40 | 20 | 60 | 40 | 20 | 60 | 40 | 20 |
| E49 | | 14 | | | 2260 | | | 21 | 21 |
| E50 | | 9 | 44 | | 1035 | 5150 | | 19 | 22 |
| E51 | | 13 | 76 | | 581 | 1790 | | 21 | 23 |
| E52 | 6 | 154 | 1560 | 236 | 595 | 2025 | 22 | 26 | 27 |

Notes)
Response speed I: speed from anti-ferroelectric state to ferroelectric state, unit $\mu$ second.
Response speed II: speed from ferroelectric state to anti-ferroelectric state, unit $\mu$ second.
Example 49: Due to defective alignment, only the response speed at 40° C. was measured.
Examples 50 and 51: The upper-limit temperature of SCA* was low so that the measurement at 60° C. was not carried out.

Examples 53 and 54

The optically active compound E1 obtained in Example 1, in an amount of 10 wt % or 50 wt %, was added to an anti-ferroelectric liquid crystal AF1, and each of the resultant compositions was measured for a phase sequence, a response speed, a tilt angle, etc., in the same manner. Tables 26 and 27 show the results.

Example 55

The optically active compound E21 obtained in Example 21, in an amount of 10 wt % or 50 wt %, was added to an anti-ferroelectric liquid crystal AF1, and the resultant compositions were evaluated for its effects. The composition containing 30 wt % of the compound E21 had an isotropic phase down to room temperature or lower, and its physical properties were unmeasurable.

Tables 26 and 27 show the physical property values of the composition containing 10 wt % of the compound E21, as Example 55.

Referential Example 2

The optically active compound E22 obtained in Example 22, in an amount of 10 wt % was added to an anti-ferroelectric liquid crystal AF1. However, the composition had an isotropic phase down to room temperature or lower, and its physical properties were unmeasurable.

TABLE 26

| Phase sequence (parenthesized values = transition temperature (° C.)) | Component | Weight ratio |
|---|---|---|
| E53 I (126) SA (107) SCY* (105) SCA* (<0) Cr | AF1/E1 | = 90/10 |
| E54 I (87) SA (60) SCY* (58) SCA* (<0) Cr | AF1/E1 | = 50/50 |
| E55 I (102) SA (101) SCY* (99) SCA* (<0) Cr | AF1/E21 | = 90/10 |

Notes)
For abbreviations, see notes to Table 18.

TABLE 27

| Measured | Response speed I | | | Response speed II | | | Tilt angle | | |
|---|---|---|---|---|---|---|---|---|---|
| temp. (° C.) | 60 | 40 | 20 | 60 | 40 | 20 | 60 | 40 | 20 |
| E53 | 783 | 834 | 1065 | 476 | 1550 | 7855 | 29 | 29 | 28 |
| E54 | | 30 | 76 | | 1265 | 5440 | | 25 | 25 |
| E55 | 94 | 187 | 361 | 385 | 1260 | 5925 | 29 | 29 | 28 |

Notes)
Response speed I: speed from anti-ferroelectric state to ferroelectric state, unit $\mu$ second.

Response speed II: speed from ferroelectric state to anti-ferroelectric state, unit $\mu$ second.

Example 54: The upper-limit temperature of SCA* was low so that the measurement at 60° C. was not carried out.

Examples 56–60

The obtained optically active compounds in E3, E4 and E5 in an amount 40 mol % each were respectively mixed with an anti-ferroelectric liquid crystal AF2 (to be referred to as "AF2" hereinafter) of the following formula, to obtain liquid crystal compositions.

Further, E5 in an amount of 30 mol % (Example 59) or 50 mol % (Example 60), was mixed with AF2 to obtain liquid crystal compositions.

AF2: n-$C_9H_{19}$—O—Ph—Ph—COO—Ph(3F)—COO—C*H(CF$_3$)(CH$_2$)$_5$OC$_2$H$_5$

In the above formula, Ph is a 1,4-phenylene group, Ph(3F) is a 1,4-phenylene group substituted with F on its 3 position (Z=F in formula (2)), and C* is asymmetric carbon.

The above-obtained anti-ferroelectric liquid crystal compositions were phase-identified and measured for response speeds, and Tables 28 and 29 show the results.

Example 61

E5 in an amount of 50 mol % was mixed with an anti-ferroelectric liquid crystal AF3 (to be referred to as "AF3" hereinafter) of the following formula, to obtain a liquid crystal composition.

AF3: n-$C_8H_{17}$—O—Ph—Ph—COO—Ph(3F)—COO—C*H(CF$_3$)(CH$_2$)$_5$OC$_2$H$_5$

In the above formula, Ph is a 1,4-phenylene group, Ph(3F) is a 1,4-phenylene group substituted with F on its 3 position (Z=F in formula (2)), and C* is asymmetric carbon.

The above-obtained anti-ferroelectric liquid crystal composition was phase-identified and measured for a response speed, and Tables 28 and 29 show the results.

As shown in Table 29, the compositions are improved particularly in response time I although both the anti-ferroelectric liquid crystals AF2 and AF3 are excellent in response speed.

TABLE 28

| | Phase sequence (parenthesized values = transition temperature (° C.)) | Component | Molar ratio |
|---|---|---|---|
| Liquid crystal | | | |
| AF2 | I (81) SC* (79) SCA* (<-50) Cr | | |
| AF3 | I (90) SCA* (<-20) Cr | | |
| E56 | I (64) SA (57) SCA* (<-20) Cr | AF2/E3 | = 60/40 |
| E57 | I (62) SA (57) SCA* (<-20) Cr | AF2/E4 | = 60/40 |
| E58 | I (60) SA (52) SC* (51) SCA* (<-20) Cr | AF2/E5 | = 60/40 |
| E59 | I (64) SA (58) SCA* (<-20) Cr | AF2/E5 | = 70/30 |
| E60 | I (58) SA (49) SCA* (<-20) Cr | AF2/E5 | = 50/50 |
| E61 | I (61) SA (50) SCA* (<-20) Cr | AF3/E5 | = 50/50 |

Notes)
For abbreviations, see notes to Table 18.

TABLE 29

| | Response speed I | Response speed II | Measured temp. (° C.) |
|---|---|---|---|
| Liquid crystal AF2 | 21 | 716 | 30 |
| Liquid crystal AF3 | 22 | 303 | 30 |
| Ex. 56 | 13 | 651 | 30 |
| Ex. 57 | 13 | 1300 | 30 |
| Ex. 58 | 15 | 1770 | 30 |
| Ex. 59 | 15 | 1285 | 30 |
| Ex. 60 | 13 | 651 | 30 |
| Ex. 61 | 13 | 296 | 30 |

Notes)

Response speed I: speed from anti-ferroelectric state to ferroelectric state, unit $\mu$ second.

Response speed II: speed from ferroelectric state to anti-ferroelectric state, unit $\mu$ second.

Examples 62–66

The optically active compounds E8, E14, E15 and E16 in an amount of 30 mol % each were mixed with a liquid crystal AF3 to obtain anti-ferroelectric liquid crystal compositions (Examples 62 to 65), and 40 mol % of the optically active compound E21 was mixed with a liquid crystal AF3 to obtain an anti-ferroelectric liquid crystal composition (Example 66). These compositions were measured for phase sequences and response times. Tables 30 and 31 show the results.

The liquid crystal AF3 itself is excellent in response time, while the compositions containing AF3 and the optically active compounds of the present invention are further improved in response time I.

TABLE 30

| | Phase sequence (parenthesized values = transition temperature (° C.)) | | | | Component | Molar ratio |
|---|---|---|---|---|---|---|
| Ex. 62 | I (65) | SA (55) | SCA* (<−20) | Cr | AF3/E8 = | 70/30 |
| Ex. 63 | I (59) | SA (47) | SCA* (<−20) | Cr | AF3/E14 = | 70/30 |
| Ex. 64 | I (65) | SC (61) | SCA* (<−20) | Cr | AF3/E15 = | 70/30 |
| Ex. 65 | I (62) | SA (51) | SCA* (<−20) | Cr | AF3/E16 = | 70/30 |
| Ex. 66 | I (55) | SCA* (<0) | Cr | | AF3/E21 = | 60/40 |

Notes)
For abbreviations, see notes to Table 18.

TABLE 31

| | Response speed I | Response speed II | Measured temp. (° C.) |
|---|---|---|---|
| Ex. 62 | 16 | 685 | 30 |
| Ex. 63 | 17 | 639 | 30 |
| Ex. 64 | 18 | 846 | 30 |
| Ex. 65 | 16 | 513 | 30 |
| Ex. 66 | 18 | 312 | 30 |

Notes)
Response speed I: speed from anti-ferroelectric state to ferroelectric state, unit $\mu$ second.
Response speed II: speed from ferroelectric state to anti-ferroelectric state, unit $\mu$ second.

Examples 67–70

The optically active compounds E17 to E20 obtained in Examples 17 to 20, in an amount of 30 wt % each, were respectively mixed with a liquid crystal AF3, and each of the resultant compositions was measured for a phase sequence and a response time. Tables 32 and 33 show the results.

Example 71

The optically active compound E11 in an amount of 30 mol % was mixed with an anti-ferroelectric liquid crystal AF4 of the following formula, to obtain a liquid crystal composition, and the composition was measured for a phase sequence and a response time. Tables 32 and 33 show the results.

AF4: n-C$_8$H$_{17}$—O—Ph—Ph—COO—Ph(3F)—COO—C*H(CF$_3$)(CH$_2$)$_7$OC$_2$H$_5$

In the above formula, Ph is a 1,4-phenylene group, Ph(3F) is a 1,4-phenylene group substituted with F on its 3 position (Z=F in formula (2)), and C* is asymmetric carbon.

Referential Examples 3 and 4

The optically active compound E11 obtained in Example 11, in an amount of 40 mol % (Referential Example 3) or 50 mol % (Referential Example 4), was mixed with the following anti-ferroelectric liquid crystal AF8, and attempts were made to measure the compositions for a phase sequence and a response time.

AF8: n-C$_8$H$_{17}$—O—Ph—Ph—COO—Ph—COO—C*H(CF$_3$)(CH$_2$)$_5$OC$_2$H$_5$

In the above formula, Ph is a 1,4-phenylene group and C* is asymmetric carbon.

Table 33 shows the phase sequences.

The compositions were unmeasurable for a response time since the crystallization proceeded during the application of voltage.

TABLE 32

| Liquid crystal | Phase sequence (parenthesized values = transition temperature (° C.)) | | | | Component | Molar ratio |
|---|---|---|---|---|---|---|
| AF3 | I (90) | SCA* (<−20) | Cr | | | |
| E67 | I (57) | SCA* (<−20) | Cr | | AF3/E17 = | 70/30 |
| E68 | I (63) | SA (49) | SCA* (<−20) | Cr | AF3/E18 = | 70/30 |
| E69 | I (59) | SCA* (<−20) | Cr | | AF3/E19 = | 70/30 |
| E70 | I (62) | SA (53) | SCA* (<−20) | Cr | AF3/E20 = | 70/30 |
| AF4 | I (77) | SCα* (76) | SCA* (<−20) | Cr | | |
| E71 | I (58) | SA (47) | SCA* (<0) | Cr | AF4/E11 = | 70/30 |
| AF8 | I (100) | SA (93) | SCA* (43) | Cr | | |
| Ref. Ex 3 | I (65) | SA (42) | SCA* (24) | Cr | AF8/E11 = | 60/40 |
| Ref. Ex 4 | I (58) | SA (33) | SCA* (16) | Cr | AF8/E11 = | 50/50 |

Notes)
For abbreviations, see notes to Table 18.

TABLE 33

| | Response speed I | Response speed II | Measured temp. (° C.) |
|---|---|---|---|
| Liquid crystal AF3 | 22 | 303 | 30 |
| E67 | 16 | 370 | 30 |
| E68 | 17 | 683 | 30 |
| E69 | 19 | 498 | 30 |
| E70 | 18 | 770 | 30 |
| Liquid crystal AF4 | 148 | 488 | 30 |
| E71 | 43 | 783 | 30 |

Notes)
Response speed I: speed from anti-ferroelectric state to ferroelectric state, unit $\mu$ second.
Response speed II: speed from ferroelectric state to anti-ferroelectric state, unit $\mu$ second.

The liquid crystal AF3 itself is excellent in response time, while the compositions containing AF3 and the optically active compounds of the present invention are further improved in response time I.

The liquid crystal AF4 has a low response time I and has a problem in practical use, while the compositions containing AF4 and the optically active compounds of the present invention are greatly improved in response time.

Examples 72–75

The optically active compounds E23 and E24 in an amount of 30 mol % each, and the optically active compounds E25 and E26 in an amount of 20 mol % each were respectively mixed with an anti-ferroelectric liquid crystal AF2 to obtain anti-ferroelectric liquid crystal compositions. The compositions were measured for phase sequences and response times, and Tables 34 and 35 show the results.

AF6: $n\text{-}C_8H_{17}\text{—}O\text{—}Ph\text{—}Ph\text{—}COO\text{—}Ph(3F)\text{—}COO\text{—}C^*H(CH_3)C_4H_9$ AF7: $n\text{-}C_8H_{17}\text{—}O\text{—}Ph\text{—}Ph\text{—}COO\text{—}Ph(3F)\text{—}COO\text{—}C^*H(CF_3)C_6H_{13}$ In the above formulae, Ph is a 1,4-phenylene group, Ph(3F) is a 1,4-phenylene group substituted with F on its 3 position (Z=F in formula (2)), and C* is asymmetric carbon.

TABLE 34

| Phase sequence (parenthesized values = transition temperature (° C.)) | | | | Component | Molar ratio |
|---|---|---|---|---|---|
| E72 I (64) | SA (53) | SCA* (<−20) | Cr | AF2/E23 = | 70/30 |
| E73 I (67) | SA (57) | SCA* (<−20) | Cr | AF2/E24 = | 70/30 |
| E74 I (66) | SA (58) | SC* (53) | SCA* (<−20) Cr | AF2/E25 = | 80/20 |
| E75 I (68) | SA (63) | SC* (62) | SCA* (<−20) Cr | AF2/E26 = | 80/20 |

Notes)
For abbreviations, see notes to Table 18.

TABLE 35

| | Response speed I | Response speed II | Measured temp. (° C.) |
|---|---|---|---|
| E72 | 37 | 2900 | 25 |
| E73 | 37 | 4600 | 25 |
| E74 | 34 | 26000 | 25 |
| E75 | 42 | 74000 | 25 |

Notes)
Response speed I: speed from anti-ferroelectric state to ferroelectric state, unit $\mu$ second.
Response speed II: speed from ferroelectric state to anti-ferroelectric state, unit $\mu$ second.

Examples 76–78

The optically active compound E11 obtained in Example 11 in an amount of 30 mol % was mixed with an anti-ferroelectric liquid crystal AF5, AF6 or AF7 of the following formula, respectively, to obtain anti-ferroelectric liquid crystal compositions. These compositions were measured for phase sequences and response times, and Tables 36 and 37 show the results.

AF5: $n\text{-}C_8H_{17}\text{—}O\text{—}Ph\text{—}Ph\text{—}COO\text{—}Ph(3F)\text{—}COO\text{—}C^*H(CH_3)C_8H_{17}$

TABLE 36

| Liquid crystal | Phase sequence (parenthesized values = transition temperature (° C.)) | | | | | | Component | Molar ratio |
|---|---|---|---|---|---|---|---|---|
| AF5 | I (131) | SA (114) | SC* (113) | SCA* (23) | SIA* (<0) | Cr | | |
| AF6 | I (149) | SA (129) | SCA* (20) | SIA* (−12) | SX (<−20) | Cr | | |
| AF7 | I (110) | SA (108) | SCA* (10) | SX (<0) | Cr | | | |
| E76 | I (96) | SA (63) | SCA* (<−10) | Cr | | | AF5/E11 = | 70/30 |
| E77 | I (106) | SA (71) | SCA* (<−10) | Cr | | | AF6/E11 = | 70/30 |
| E78 | I (86) | SA (72) | SCA* (<−10) | Cr | | | AF7/E11 = | 70/30 |

Notes)
For abbreviations, see notes to Table 18.
SX: Unidentified liquid crystal phase.

TABLE 37

| | Response speed I | Response speed II | Tilt angle | Measured temp. (° C.) |
|---|---|---|---|---|
| Liquid crystal AF5 | 351 | 1430 | 29 | 30 |
| Liquid crystal AF6 | −*1 | −*1 | 30 | 30 |
| Liquid crystal AF7 | −*1 | −*1 | 37 | 30 |
| E76 | 26 | 2645 | 23 | 30 |
| E77 | 148 | 3370 | 23 | 30 |
| E78 | 38 | 867 | 31 | 30 |

Notes)
Response speed I: speed from anti-ferroelectric state to ferroelectric state, unit $\mu$ second.
Response speed II: speed from ferroelectric state to anti-ferroelectric state, unit $\mu$ second.
*1: Threshold voltage was very high, as high as 20 V/mm or more, so that the response time was unmeasurable under measurement conditions.

Examples 79–85

The two-rings-containing phenyl ester compounds E27 to E33 obtained in Examples 27 to 33, in an amount of 30 mol % in each of E27 and E29 to E33 or 35 mol % in E28, were mixed with a liquid crystal AF2, to obtain anti-ferroelectric liquid crystal compositions. The Compositions were measured for phase sequences and response times, and Tables 38 and 39 show the results.

TABLE 38

| | Phase sequence (parenthesized values = transition temperature (° C.)) | Component | Molar ratio |
|---|---|---|---|
| Liquid crystal | | | |
| AF2 | I (83) SC* (77) SCA* (<−50) Cr | | |
| E79 | I (85) SA (71) SC* (65) SCA* (<−20) Cr | AF2/E27 | = 70/30 |
| E80 | I (84) SA (73) SC* (65) SCA* (<−20) Cr | AF2/E28 | = 65/35 |
| E81 | I (79) SA (59) SCA* (<−20) Cr | AF2/E29 | = 70/30 |
| E82 | I (81) SA (62) SCA* (<−20) Cr | AF2/E30 | = 70/30 |
| E83 | I (82) SA (70) SCA* (<−20) Cr | AF2/E31 | = 70/30 |
| E84 | I (82) SA (72) SCA* (<−20) Cr | AF2/E32 | = 70/30 |
| E85 | I (86) SA (70) SCA* (<−20) Cr | AF2 E33 | = 70 30 |

Notes)
For abbreviations, see notes to Table 18.

TABLE 39

| | Response speed I | Response speed II | Measured temp.(° C.) |
|---|---|---|---|
| Liquid crystal AF2 | 79 | 2020 | 10 |
| E79 | 64 | 8500 | 10 |
| E80 | 61 | 6600 | 10 |
| E81 | 64 | 9600 | 10 |
| E82 | 67 | 8100 | 10 |
| E83 | 51 | 1200 | 10 |
| E84 | 72 | 7500 | 10 |
| E85 | 71 | 3300 | 10 |

Notes)
Response speed I: speed from anti-ferroelectric state to ferroelectric state, unit second.
Response speed II: speed from ferroelectric state to anti-ferroelectric state, unit second.

As is clearly shown in Tables 38 and 39, the liquid crystal AF2 has no smectic A phase, while there are obtained compositions having a smectic A phase by incorporating the two-rings-containing phenyl ester compounds. Further, the compositions retain an anti-ferroelectric phase in a broad temperature range and are improved in response time I at 10° C.

What is claimed is:

1. A two-ringed phenyl ester compound of the following general formula (1)

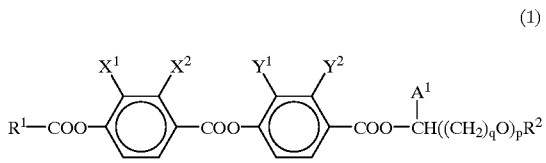

wherein $R^1$ is a linear alkyl group having 5 to 12 carbon atoms, $R^2$ is a linear alkyl group having 1 to 15 carbon atoms, $X^1$ and $X^2$ are both hydrogen atoms or one of $X^1$ and $X^2$ is a fluorine atom and the other is a hydrogen atom, $Y^1$ and $Y^2$ are both hydrogen atoms or one of $Y^1$ and $Y^2$ is a fluorine atom and the other is a hydrogen atom, and $A^1$ is —$CH_3$ or —$CF_3$, provided that when $A^1$ is —$CH_3$, p is 0, and that when $A^1$ is —$CF_3$, p is 1 and q is an integer of 5 to 8.

2. The two-ringed phenyl ester compound of claim 1, wherein the two-ringed phenyl ester compound has the general formula (1) in which $R^1$ is a linear alkyl group having 8 to 12 carbon atoms.

3. The two-ringed phenyl ester compound of claim 1, wherein the two-ringed phenyl ester compound is optically active and has the general formula (1) in which $A^1$ is —$CH_3$, p is 0 and $R^2$ is a linear alkyl group having 3 to 8 carbon atoms.

4. The two-ringed phenyl ester compound of claim 1, wherein the two-ringed phenyl ester compound is optically active and has the general formula (1) in which $A^1$ is —$CF_3$, p is 1, q is 5 and $R^2$ is ethyl.

* * * * *